US005605877A

United States Patent [19]

Schafer et al.

[11] Patent Number: 5,605,877

[45] Date of Patent: Feb. 25, 1997

[54] BICYCLIC IMIDES AS HERBICIDES

[75] Inventors: Matthias Schafer, Haibach; Karlheinz Drauz, Freigericht; Dieter Feit, Wachtersbach, all of Germany; Kofi S. Amuti, Wilmington, Del.

[73] Assignee: E. I. Du Pont de Nemours and Company, Wilmington, Del.

[21] Appl. No.: 397,282

[22] PCT Filed: Sep. 6, 1993

[86] PCT No.: PCT/EP93/02413

§ 371 Date: Mar. 10, 1995

§ 102(e) Date: Mar. 10, 1995

[87] PCT Pub. No.: WO94/05668

PCT Pub. Date: Mar. 17, 1994

Related U.S. Application Data

[63] Continuation-in-part of Ser. No. 942,800, Sep. 10, 1992, abandoned.

[51] Int. Cl.$^6$ .......................... A01N 43/90; C07D 487/04

[52] U.S. Cl. ....................... 504/266.2; 504/193; 504/197; 548/110; 548/113; 548/302.7

[58] Field of Search .................................... 548/110, 113, 548/302.7; 504/193, 197, 276

[56] References Cited

U.S. PATENT DOCUMENTS

| | | | |
|---|---|---|---|
| 3,948,933 | 4/1976 | Fontanella | 548/302.7 |
| 5,482,921 | 1/1996 | Seckinger et al. | 504/246 |

*Primary Examiner*—Patricia L. Morris

[57] ABSTRACT

Compounds of Formula I are disclosed which are useful for controlling undesired vegetation

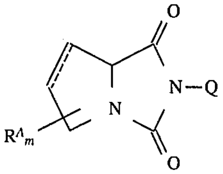

I wherein

Q is

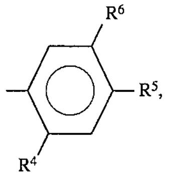

Q-1

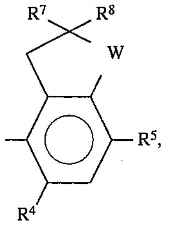

Q-2

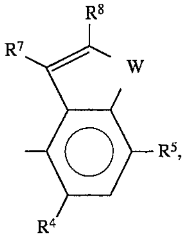

Q-3

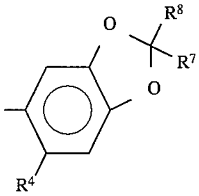

Q-6 or

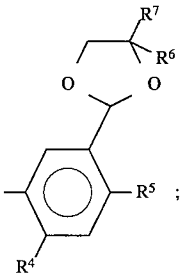

Q-7 and W, $R^A{}_m$, $R^4$–$R^8$ are as defined in the disclosure.

Also disclosed are compositions containing the compounds of Formula I and a method for controlling undesired vegetation which involves contacting the vegetation or its environment with an effective amount of a compound of Formula I.

11 Claims, No Drawings

BICYCLIC IMIDES AS HERBICIDES

This application is a Sec. 371 application of PCT application number PCT/EP93/02413, filed 06 Sep. 1993, which is a continuation-in-part of U.S. application Ser. No. 07/942,800, filed 10 Sep. 1992, now abandoned.

DESCRIPTION

This invention relates to novel bicyclic imides; a method for their preparation; and their use as herbicides.

It has already been disclosed that certain heterocyclic imides (see EP-A 272 594, EP-A 493 323, EP-B 0 070 389, EP-B 0 104 532) can be employed as herbicides.

Now novel bicyclic imides have been found that exhibit markedly better herbicidal activity with excel-lent selectivity.

The subject of the present invention therefore comprises compounds of formula I

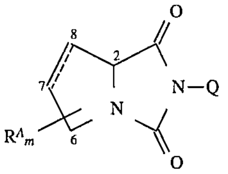

I wherein the bond linking C-7 and C-8 may be single or double;

m is 1–7;

$R^A$ can occupy one or more of the 2 or 6–8 positions and is independently selected from the group: hydroxy, halogen, CN, $OR^3$, $(C_1–C_4)$alkyl, $S(O)_nR^3$, $COR^3$, $C(O)SR^3$ and $C(O)NR^{11}R^{12}$;

Q is

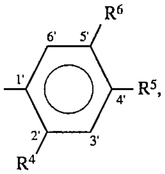

Q-1

Q-1

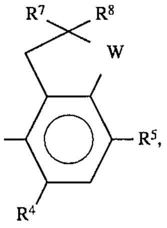

Q-2

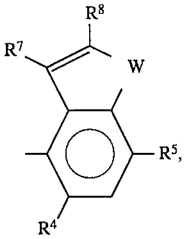

Q-3

-continued

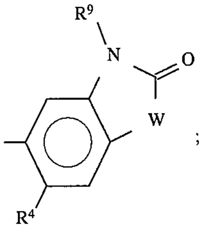

Q-4

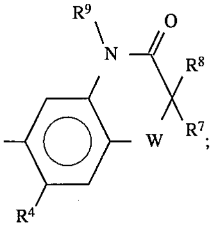

Q-5

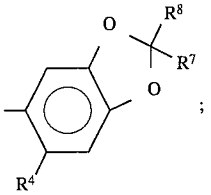

Q-6

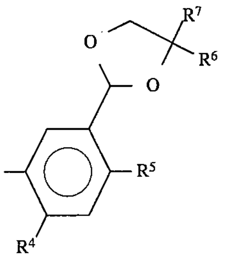

Q-7 wherein $R^3$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_4)$carboxy alkyl, $(C_3–C_8)$alkoxycarbonylalkyl, $(C_4–C_8)$alkenyloxyalkyl, $(C_4–C_6)$alkynyloxyalky, $(C_3–C_8)$haloalkoxyalkyl, $(C_3–C_8)$ trialkylsilyl, $(C_3–C_8)$cyanoalkyl, $(C_3–C_8)$haloalkenyl, $(C_3–C_8)$haloalkynyl, $(C_2–C_8)$alkylcarbonyl, $(C_2–C_8)$alkoxycarbonyl, $(C_2–C_8)$haloalkoxycarbonyl, $P(O)(OR^{17})_2$, $CHR^{16}P(O)(OR^{17})_2$ or $CHR^{16}P(S)(OR^{17})_2$, phenyl or benzyl optionally substituted with halogen, $(C_1–C_3)$alkyl, $(C_1–C_3)$haloalkyl or $(C_1–C_4)$alkoxy;

$R^4$ is hydrogen or halogen;

$R^5$ is $(C_1–C_2)$alkyl, $(C_1–C_2)$haloalkyl, $OCH_3$, $SCH_3$, $OCHF_2$, halogen, CN or $NO_2$;

$R^6$ is hydrogen, $(C_1–C_8)$alkyl, $(C_1–C_8)$haloalkyl. halogen, $OR^{10}$, $S(O)_nR^{10}$, $COR^{10}$, $C(O)SR^{10}$, $C(O)NR^{11}R^{12}$, CHO, $CH{=}CHCO_2R^{10}$, $CO_2N{=}CR^{13}R^{14}$, $NO_2$, CN, $NHSO_2R^{15}$ or $NHSO_2NHR^{15}$;

$R^7$ and $R^3$ are independently hydrogen, $(C_1–C_3)$alkyl. $(C_1–C_3)$haloalkyl or halogen; when Q is Q-2 or Q-6, $R^1$ and $R^8$ together with the carbon to which they are attached may be C=O;

$R^9$ is $(C_1–C_6)$alkyl, $(C_1–C_6)$haloalkyl, $(C_2–C_6)$alkoxyalkyl, $(C_3–C_6)$alkenyl or $(C_3–C_6)$alkynyl;

$R^{10}$ is $(C_1–C_8)$alkyl. $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_6)$alkylthioalkyl, $(C_2-C_8)$alkylsulfinylalkyl, $(C_2-C_8)$alkylsulfonylalkyl, $(C_3-C_8)$alkoxyalkoxyalkyl, $(C_4-C_8)$cycloalkylalkyl, $(C_2-C_4)$carboxyalkyl, $(C_3-C_8)$alkoxycarbonylalkyl, $(C_6-C_8)$alkenyloxycarbonylalkyl, $(C_6-C_8)$alkynyloxycarbonylalkyl, $(C_6-C_8)$cycloalkoxyalkyl, $(C_4-C_8)$alkenyloxyalkyl, $(C_4-C_8)$alkynyloxyalkyl, $(C_3-C_8)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_3-C_8)$cyanoalkyl, $(C_3-C_8)$halocycloalkyl, $(C_3-C_8)$haloalkenyl, $(C_5-C_3)$alkoxyalkenyl, $(C_5-C_8)$haloalkoxyalkenyl, $(C_5-C_8)$alkylthioalkenyl, $(C_3-C_8)$haloalkynyl, $(C_5-C_8)$alkoxyalkynyl, $(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}p(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1-C_4)$alkyl substituted with phenoxy or benzyloxy optionally substituted with halogen, $(C_1-C_3)$alkyl or $(C_1-C_3)$haloalkyl; benzyl optionally substituted with halogen, $(C_1-C_3)$alkyl or $(C_1-C_3)$haloalkyl; or phenyl and pyridyl optionally substituted with halogen, $(C_1-C_3)$alkyl, $(C_1-C_3)$haloalkyl or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, or phenyl optionally substituted with halogen, $(C_1-C_3)$alkyl, $(C_1-C_3)$haloalkyl or $(C_1-C_4)$alkoxy;

$R^{11}$ and $R^{12}$ may be taken together: as $—(CH_2)_5—$, $—(CH_2)_4—$ or $—CH_2CH_2OCH_2CH_2—$, in which optionally one or more H-atoms may be replaced by $(C_1-C_3)$alkyl, phenyl or benzyl;

$R^{13}$ and $R^{14}$ may be taken together with the carbon to which they are attached to form $(C_3-C_8)$cycloalkyl;

$R^{15}$ is $(C_1-C_4)$alkyl or $(C_1-C_4)$haloalkyl;

$R^{16}$ is hydrogen or $(C_1-C_3)$alkyl $R^{17}$ is $(C_1-C_6)$alkyl, $(C_3-C_6)$alkenyl or $(C_3-C_6)$alkynyl;

W is O or S;

n is O or 2; provided that when Q is not fused to a ring bridging the 5'- and 6=-position and C-7 and C-8 are linked by a single bond, then at least one $R^A$ is other than hydroxy, halogen, $(C_1-C_4)$alkyl and $(C_1-C_4)$alkoxy.

The subject of the present invention comprises further bicyclic imides selected from the group consisting of 4-[4'-chloro-2'-fluoro-5'-(prop-2- ynyloxy)phenyl]-3,5-dioxo-7-fluoro-1,4-diazabicyclo-[3.3.0]octane, 4-[4'-chloro-2'-fluoro-5'-(1-methyl-prop-2-ynyloxy)phenyl]-3,5-dioxo-7-fluoro-1,4-diazabicyclo[3.3.0]octane, 4-[4'-chloro-2'-fluoro-5'-(2-propynyloxy)phenyl]-3,5-dioxo-7-chloro-1,4-diazabicyclo[3.3.0]octane, 4-[4'-chloro-2'-fluoro-5'-(1-methyl-ethoxy)phenyl]-3,5-dioxo-7,7-difluoro-1,4-diazabicyclo[3.3.0]octane and stereoisomers thereof.

In the above definitions, the term "alkyl", used either alone or in compound words such as "alkylthio" or "haloalkyl", includes straight Chain or branched alkyl, e.g., methyl, ethyl, n-propyl, isopropyl or the different butyl isomers. Alkoxy includes e.g. methoxy, ethoxy, n-propyloxy, isopropyloxy and the different butoxy isomers. Alkenyl includes straight chain or branched alkenes, e.g., 1-propenyl, 2-propenyl, 3-propenyl and the different butenyl isomers. Cycloalkyl includes e.g. cyclopropyl, cyclobutyl, cyclopentyl and cyclohexyl. The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

More preferred are compounds of formula I having at least one of the following specifications $R^3$ is p referred $(C_1-C_4)$alkyl, $(C_3-C_6)$cycloalkyl, $(C_3-C_6)$alkenyl, $(C_3-C_6)$alkynyl, $(C_1-C_4)$haloalkyl, $(C_2-C_6)$alkoxyalkyl: $(C_2-C_4)$carboxyalkyl, $(C_3-C_6)$alkoxycarbonylalkyl, $(C_4-C_6)$alkenyloxyalkyl, $(C_1-C_6)$alkynyloxyalkyl, $(C_3-C_6)$haloalkoxyalkyl, $(C_3-C_6)$trialkylsilyl, $(C_3-C_6)$cyanoalkyl, $(C_3-C_6)$haloalkenyl, $(C_3-C_6)$haloalkynyl, $(C_2-C_6)$alkylcarbonyl, $P(O)(OR^{17})_2$, $(C_2-C_6)$alkoxycarbonyl, $(C_2-C_6)$haloalkoxycarbonyl, $CHR^{16}P(O)(OR^{17})_2$ or $CHR^{16}P(S)(OR^{17})_2$, phenyl or benzyl optionally substituted with halogen, $(C_1-C_3)$alkyl, $(C_1-C_3)$haloalkyl or $(C_1-C_4)$alkoxy;

$R^5$ is halogen or CN;

$R^6$ is hydrogen, $(C_1-C_4)$alkyl, $(C_1-C_4)$haloalkyl, halogen, $OR^{10}$, $S(O)_nR^{10}$, $COR^{10}$, $CO_2R^{10}$, $C(O)SR^{10}$, $C(O)NR^{11}R^{12}$, $CH{=}CHCO_2R^{10}$, $CO_2N{=}CR^{13}R^{14}$, $NHSO_2R^{15}$ or NHSO $NHR^{15}$;

$R^7$ and $R^8$ are independently hydrogen, $(C_1-C_3)$alkyl or $(C_1-C_3)$haloalkyl; when Q is Q-2 or Q-6, $R^7$ and $R^8$ together with the carbon to which they are attached may be C=O;

$R^9$ is $(C_1-C_4)$alkyl, $(C_1-C_4)$haloalkyl, $(C_2-C_4)$alkoxyalkyl, $(C_3-C_6)$alkenyl or $(C_3-C_6)$alkynyl;

$R^{10}$ is $(C_1-C_4)$alkyl, $(C_3-C_6)$cycloalkyl, $(C_3-C_6)$alkenyl, $(C_3-C_6)$alkynyl, $(C_1-C_4)$haloalkyl, $(C_2-C_4)$alkoxyalkyl, $(C_2-C_4)$alkylthioalkyl, $(C_2-C_4)$alkylsulfinylalkyl, $(C_2-C_4)$alkylsulfonylalkyl, $(C_3-C_6)$alkoxyalkoxyalkyl, $(C_4-C_8)$cycloalkylalkyl, $(C_2-C_4)$carboxyalkyl, $(C_3-C_6)$alkoxycarbonylalkyl, $(C_6-C_8)$alkenyloxycarbonylalkyl, $(C_6-C_8)$alkynyloxycarbonylalkyl, $(C_6-C_8)$cycloalkoxyalkyl, $(C_1-C_6)$alkenyloxyalkyl, $(C_4-C_6)$alkynyloxyalkyl, $(C_3-C_6)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_6)$alkenylthioalkyl, $(C_1-C_6)$alkynylthioalkyl, $(C_4-C_8)$trialkylsilylalkyl, $(C_3-C_4)$cyanoalkyl, $(C_3-C_6)$halocycloalkyl, $(C_3-C_6)$haloalkenyl, $(C_5-C_6)$alkoxyalkenyl, $(C_5-C_6)$haloalkoxyalkenyl, $(C_5-C_6)$alkylthioalkenyl, $(C_3-C_6)$haloalkynyl, $(C_5-C_6)$alkoxyalkynyl, $(C_5-C_6)$haloalkoxyalkynyl, $(C_5-C_6)$alkylthioalkynyl, $(C_2-C_4)$alkyl carbonyl, $CHR^{16}COR^{17}$, $CHR^{16}P(O)(OR^{17})_2$, $P(O)(OR^{17})_2$, $CHR^6P(S)(OR^{17})_2$, $CHR^{16}C(O)NR^{11}R^{12}$, $CHR^{16}C(O)NH_2$, $(C_1-C_2)$alkyl substituted with phenoxy or benzyloxy optionally substituted with halogen. $(C_1-C_3)$alkyl or $(C_1-C_3)$haloalkyl; benzyl optionally substituted with halogen, $(C_1-C_2)$alkyl or $(C_1-C_2)$haloalkyl; or phenyl and pyridyl optionally substituted with halogen, $(C_1-C_3)$alkyl, $(C_1-C_3)$haloalkyl or $(C_1-C_4)$alkoxy;

$R^{12}$ and $R^{14}$ are independently $(C_1-C_2)$alkyl, phenyl optionally substituted with halogen. $(C_1-C_2)$alkyl, $(C_1-C_2)$haloalkyl or $(C_1-C_2)$alkoxy;

$R^{11}$ and $R^{12}$ may be taken together as $—(CH_2)_5—$, $—(CH_2)_4—$ or $—CH_2CH_2OCH_2CH_2—$, each ring optionally substituted with $(C_1-C_2)$alkyl, phenyl or benzyl;

$R^{13}$ and $R^{14}$ may be taken together with the carbon to which they are attached to form $(C_3-C_6)$cycloalky;

$R^{17}$ is $(C_1-C_4)$alkyl, $(C_3-C_6)$alkenyl or $(C_3-C_6)$alkynyl.

Compounds having a substituted proline residue, particularly in 7-position, exibit a beneficial effect on undesired plants, preferred are fluoro, bromo or chloro.

Particularly preferred method of use employs compounds of formula II

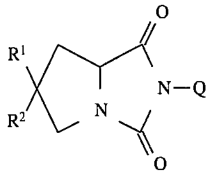

II in which $R^1$ is halogen $(C_1-C_4)$alkyl $OR^3$, $S(O)_nR^3$, $COR^3$, $CO_2R^3$ $C(O)SR^3$ $C(O)NR^{11}R^{12}$ or CN;

$R^2$ is hydrogen, halogen, $(C_1-C_4)$alkyl, $OR^3$, $S(O)_nR^3$, $COR^3$, $CO_2R^3$ $C(O)SR^3$ $C(O)NR^{11}R^{12}$ or CN;

Especially preferred method of use employs compounds of formula II in which at least one of $R^1$–$R^3$ has the meaning $R^1$=hydrogen or $(C_1-C_4)$alkyl;

$R^2$=fluoro, chloro, bromo, $OR^3$, $S(O)_nR^3$, $CO_2R^3$, $C(O)NR^{11}R^{12}$ or CN;

$R^3$=$(C_1-C_4)$alkyl, $(C_3-C_6)$cycloalkyl, $(C_3-C_6)$alkenyl, $(C_3-C_6)$alkynyl, $(C_1-C_4)$haloalkyl or $(C_3-C_6)$trialkylsilyl.

Most preferred method of use employ compounds of formula II with at least one of the following specifications $R^1$=hydrogen, $R^2$=fluoro, chloro, bromo or $OR^3$, $R^3$=$(C_1-C_2)$alkyl, $(C_1-C_2)$haloalkyl, and in Q $R^4$ is fluoro or chloro;

$R^5$ is chloro;

$R^6$ is $OR^{10}$, $CO_2R^{10}$, $NHSO_2R^{10}$ or $SR^{10}$;

$R^7$ is hydrogen;

$R^8$ is hydrogen or methyl;

$R^9$ is $(C_3-C_4)$alkenyl or $(C_3-C_4)$alkynyl;

$R^{10}$ is $(C_1-C_4)$alkyl, $(C_3-C_6)$cycloalkyl, $(C_3-C_6)$alkenyl $(C_3-C_4)$alkynyl, $(C_1-C_3)$haloalkyl, $(C_2-C_4)$alkoxyalkyl, $(C_3-C_6)$alkoxycarbonylalkyl, $(C^6-C^8)$alkenyloxycarbonylalkyl, $(C^6-C^8)$alkynyloxycarbonylalkyl or $(C^1-C^2)$carboxyalkyl.

If not otherwise specified the invention relates to both the individual possible stereoisomers of formula I and II and also mixtures of the isomers. Stereoisomers exhibiting the 2R-configuration are preferred to others.

The 2R-configuration exhibits significantly better control, e.g. up to 8-fold, compared with the 2S-configuration on undesired plants.

Subject of the invention is also a method for preparing the novel bicyclic imides comprising:

(a) reacting a compound of formula III

Q—NCO III with a compound of formula IV

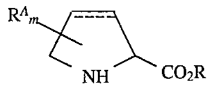

IV wherein R=H or $(C_1-C_4)$alkyl, and cyclizing the intermediate and a method for preparing bicyclic imides of formula Ia

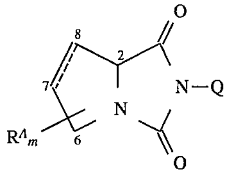

Ia wherein the bond linking C-7 and C-8 may be single or double:

m is 1–7;

$R^A$ can occupy one or more of the 2 or 8–8 positions and is independently selected from the group: hydroxy, halogen, CN, $OR^3$, $(C_1-C_4)$alkyl. $S(O)_nR^3$, $COR^3$, $C(O)SR^3$ and $C(O)NR^{11}R^{12}$;

Q is

Q is

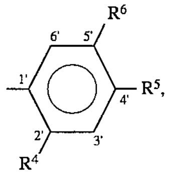

Q-1

Q-1

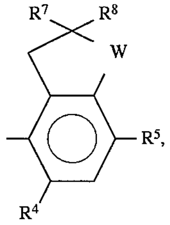

Q-2

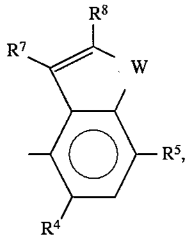

Q-3

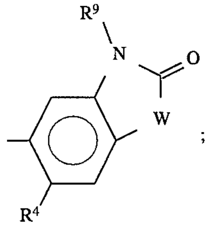

Q-4

-continued

Q-5

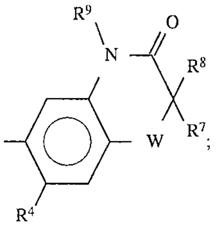

Q-6

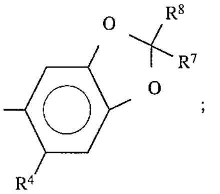

Q-7

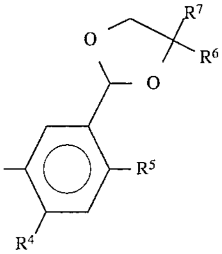

wherein $R^3$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_4)$carboxyalkyl, $(C_3–C_8)$alkoxycarbonylalkyl, $(C_4–C_8)$alkenyloxyalkyl, $(C_4–C_8)$alkynyloxyalkyl, $(C_3–C_8)$haloalkoxyalkyl, $(C_3–C_8)$trialkylsilyl, $(C_3–C_8)$cyanoalkyl, $(C_3–C_8)$haloalkenyl, $(C_3–C_8)$haloalkynyl, $(C_2–C_8)$alkylcarbonyl, $(C_2–C_8)$alkoxycarbonyl, $(C_2–C_8)$haloalkoxycarbonyl, $P(O)(OR^{17})_2$, $CHR^{16}P(O)IOR^{17})_2$ or $CHR^{16}P(S)(OR^{17})_2$, phenyl or benzyl optionally substituted with halogen, $(C_1–C_3)$alkyl. $(C_1–C_3)$haloalkyl or $(C_1–C_4)$alkoxy;

$R^4$ is hydrogen or halogen;

$R^5$ is $(C_1–C_2)$alkyl, $(C_1–C_2)$haloalkyl, $OCH_3$, $SCH_3$, $OCHF_2$, halogen, CN or $NO_2$;

$R^6$ is hydrogen, $(C_1–C_8)$alkyl, $(C_1–C_8)$haloalkyl, halogen, $OR^{10}$, $S(O)_nR^{10}$, $COR^{10}$, $C(O)SR^{10}$, $C(O)NR^{11}R^{12}$, CHO, $CH{=}CHCO_2R^{10}$, $CO_2N{=}CR^{13}R^{14}$, $NO_2$, CN, $NHSO_2R^{15}$ or $NHSO_2NHR^{15}$;

$R^7$ and $R^8$ are independently hydrogen, $(C_1–C_3)$alkyl, $(C_1–C_3)$haloalkyl or halogen; when Q is Q-2 or Q-6, $R^7$ and $R^8$ together with the carbon to which they are attached may be C=O;

$R^9$ is $(C_1–C_8)$alkyl, $(C_1–C_6)$haloalkyl, $(C_2–C_6)$alkoxyalkyl, $(C_3–C_6)$alkenyl or $(C_3–C_6)$alkynyl;

$R^{10}$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_6)$alkylthioalkyl, $(C_2–C_8)$alkylsulfinylalkyl, $(C_2–C_8)$alkylsulfonylalkyl, $(C_3–C_8)$alkoxyalkoxyalkyl, $(C_4–C_8)$cycloalkylalkyl, $(C_2–C_4)$carboxyalkyl, $(C_3–C_8)$alkoxycarbonylalkyl, $(C_6–C_8)$alkenyloxycarbonylalkyl, $(C_6–C_8)$alkynyloxycarbonylalkyl, $(C_6–C_8)$cycloalkoxyalkyl, $(C_4–C_8)$alkenyloxyalkyl, $(C_4–C_8)$alkynyloxyalkyl, $(C_3–C_8)$haloalkoxyalkyl, $(C_4–C_8)$haloalkenyloxyalkyl, $(C_4–C_8)$haloalkynyloxyalkyl, $(C_6–C_8)$cycloalkylthioalkyl, $(C_4–C_8)$alkenylthioalkyl, $(C_4–C_8)$alkynylthioalkyl, $(C_4–C_8)$trialkylsilylalkyl, $(C_3–C_8)$cyanoalkyl, $(C_3–C_8)$halocycloalkyl, $(C_3–C_8)$haloalkenyl, $(C_5–C_8)$alkoxyalkenyl, $(C_5–C_8)$haloalkoxyalkenyl, $(C_5–C_8)$alkylthioalkenyl, $(C_3–C_8)$haloalkynyl, $(C_5–C_8)$alkoxyalkynyl, $(C_5–C_8)$haloalkoxyalkynyl, $(C_5–C_8)$alkylthioalkynyl, $(C_2–C_8)$alkylcarbonyl, $CHR^{16}COR^{17}$, $CHR^{15}p(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1–C_4)$alkyl substituted with phenoxy or benzyloxy optionally substituted with halogen, $(C_1–C_3)$alkyl or $(C_1–C_3)$haloalkyl; benzyl optionally substituted with halogen, $(C_1–C_3)$alkyl or $(C_1–C_3)$haloalkyl; or phenyl and pyridyl optionally substituted with halogen, $(C_1–C_3)$alkyl, $(C_1–C_3)$haloalkyl or $(C_1–C_4)$alkoxy;

$R^{11}$ and $R^{13}$ are independently hydrogen or $(C_1–C_4)$alkyl;

$R^{12}$ and $R^{14}$ are independently $(C_1–C_4)$alkyl, or phenyl optionally substituted with halogen, $(C_1–C_3)$alkyl, $(C_1–C_3)$haloalkyl or $(C_1–C_4)$alkoxy;

$R^{11}$ and $R^{12}$ may be taken together as $—(CH_2)_5—$, $—(CH_2)_4—$ or $—CH_2CH_2OCH_2CH_2—$, in which optionally one or more H-atoms may be replaced by $(C_1–C_3)$alkyl, phenyl or benzyl;

$R^{13}$ and $R^{14}$ may be taken together with the carbon to which they are art ached to form $(C_3–C_8)$cycloalkyl;

$R^{15}$ is $(C_1–C_4)$alkyl or $(C_1–C_4)$haloalkyl;

$R^{16}$ is hydrogen or $(C_1–C_8)$alkyl;

$R^{17}$ is $(C_1–C_6)$alkyl, $(C_3–C_6)$alkenyl or $(C_3–C_6)$alkynyl;

W is O or S;

n is 0, 1 or 2;

selected from the group consisting ;of (b) or (c):

(b) reacting a compound of formula IV, wherein R=H or $(C_1–C_4)$alkyl, with phosgene and then with an amine of formula VI $$Q—NH_2 \qquad \text{VI}$$

to form compounds of formula VII,

VII

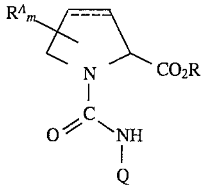

and cyclizing the compounds of formula VII, or (c) reacting a compound of formula III with a compound of formula VIII

VIII

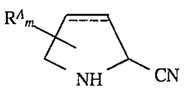

to form a compound of formula IX,

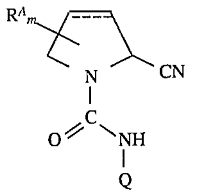

IX and hydrolyzing and cylizing the compound of formula IX.

The novel bicyclic imides can be produced in a method comprising preparing a compound of formula II

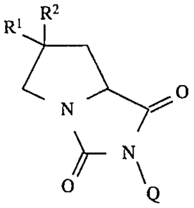

II wherein $R^1$ is $R^A$ $R^2$ is $R^A$ and H comprising reacting a compound of formula X,

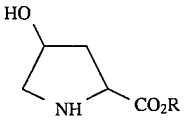

X wherein R=H or $(C_1-C_4)$alkyl, with a compound of general formula III

Q—NCO III and converting the reaction product formed thereby.

Subject of the invention is further a method for making compounds of formula Ia

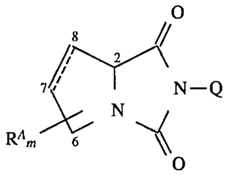

Ia wherein the bond linking C-7 and C-8 may be single or double;

m is 1–7;

$R^A$ can occupy one or more of the 2 or 6–8 positions and is independently selected from the group: hydroxy, halogen, CN, $OR^3$, $(C_1-C_4)$alkyl, $S(O)_nR^3$, $COR^3$, $C(O)SR^3$ and $C(O)NR^{11}R^{12}$;

Q is

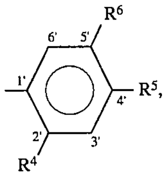

Q-1

Q-1

-continued

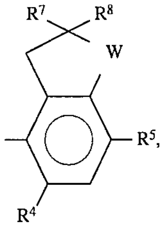

Q-2

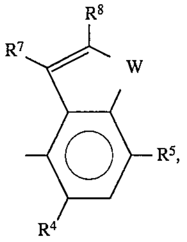

Q-3

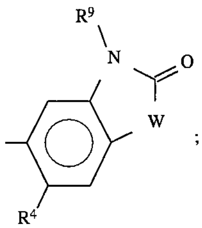

;

Q-4

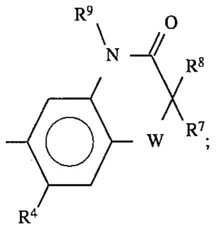

Q-5

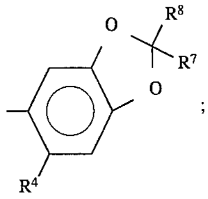

;

Q-6

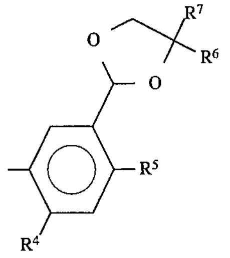

Q-7 wherein $R^3$ is $(C_1-C_8)$alkyl, $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_4)$carboxyalkyl, $(C_3-C_8)$alkoxycarbonylalkyl, $(C_4-C_8)$alkenyloxyalkyl, $(C_4-C_8)$alkynyloxyalkyl, $(C_3-C_8)$haloalkoxyalkyl, $(C_3-C_8)$trialkylsilyl, $(C_3-C_8)$cyanoalkyl, $(C_3-C_8)$haloalkenyl, $(C_3-C_8)$haloalkynyl, $(C_2-C_8)$alkylcarbonyl, $(C_2-C_8)$alkoxycarbonyl, $(C_2-C_8)$haloalkoxycarbonyl, $P(O)(OR^{17})_2$, $CHR^{16}P(O)(OR^{17})_2$ or $CHR^{16}P(S)(OR^{17})_2$, phenyl or benzyl optionally substituted with halogen, $(C_1-C_3)$alkyl, $(C_1-C_3)$haloalkyl or $(C_1-C_4)$alkoxy;

$R^4$ is hydrogen or halogen;

$R^5$ is $(C_1-C_2)$alkyl, $(C_1-C_2)$haloalkyl, $OCH_3$, $SCH_3$, $OCHF_2$, halogen, CN or $NO_2$;

$R^6$ is $OR^{10}$, $S(O)_nR^{10}$, $NHSO_2R^{15}$ or $NHSO_2NHR^{15}$;

$R^7$ and $R^8$ are independently hydrogen, $(C_1-C_3)$alkyl, $(C_1-C_3)$haloalkyl or halogen; when Q is Q-2 or Q-6, $R^7$ and $R^8$ together with the carbon to which they are attached may be C═O;

$R^9$ is $(C_1-C_6)$alkyl, $(C_1-C_6)$haloalkyl, $(C_2-C_6)$alkoxyalkyl, $(C_3-C_6)$alkenyl or $(C_3-C_6)$alkynyl;

$R^{10}$ is $(C_1-C_8)$alkyl, $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_6)$alkylthioalkyl, $(C_2-C_8)$alkylsulfinylalkyl, $(C_2-C_8)$alkylsulfonylalkyl, $(C_3-C_8)$alkoxyalkoxyalkyl, $(C_4-C_8)$ cycloalkylalkyl, $(C_2-C_4)$carboxyalkyl, $(C_3-C_8)$alkoxycarbonylalkyl, $(C_6-C_8)$alkenyloxycarbonylalkyl, $(C_6-C_8)$alkynyloxycarbonylalkyl, $(C_6-C_8)$cycloalkoxyalkyl, $(C_4-C_8)$alkenyloxyalkyl, $(C_4-C_8)$alkynyloxyalkyl, $(C_3-C_8)$ haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_3-C_8)$cyanoalkyl, $(C_3-C_8)$halocycloalkyl, $(C_3-C_8)$haloalkenyl, $(C_5-C_8)$alkoxyalkenyl, $(C_5-C_8)$haloalkoxyalkenyl, $(C_5-C_8)$alkylthioalkenyl, $(C_3-C_8)$haloalkynyl, $(C_5-C_8)$alkoxyalkynyl, $(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1-C_4)$alkyl substituted with phenoxy or benzyloxy optionally substituted with halogen, $(C_1-C_3)$alkyl or $(C_1-C_3)$haloalkyl; benzyl optionally substituted with halogen, $(C_1-C_3)$alkyl or $(C_1-C_3)$haloalkyl; or phenyl and pyridyl optionally substituted with halogen. $(C_1-C_3)$alkyl, $(C_1-C_3)$haloalkyl or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, or phenyl optionally substituted with halogen, $(C_1-C_3)$alkyl, $(C_1-C_3)$haloalkyl or $(C_1-C_4)$alkoxy;

$R^{11}$ and $R^{12}$ may be taken together as $-(CH_2)_5-$, $-(CH_2)_4-$ or $-CH_2CH_2OCH_2CH_2-$, in which optionally one or more H-atoms may be replaced by $(C_1-C_3)$alkyl, phenyl or benzyl;

$R^{13}$ and $R^{14}$ may be taken together with the carbon to which they are attached to form $(C_3-C_8)$cycloalkyl;

$R^{15}$ is $(C_1-C_4)$alkyl or $(C_1-C_4)$haloalkyl;

$R^{16}$ is hydrogen or $(C_1-C_3)$alkyl;

$R^{17}$ is $(C_1-C_6)$alkyl, $(C_3-C_6)$alkenyl or $(C_3-C_6)$alkynyl;

W is 0 or S;

n is 0, 1 or 2:

comprising reacting a compound of the formula XIII

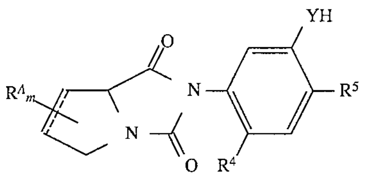

XIII wherein Y=0, S, NH with a halide selected from the group $R^{10}$—Z, $R^{15}SO_2$—Z, and $R^{15}NHSO_2$—Z wherein Z is chlorine, bromine or iodine.

The novel bicyclic imides of general formula I are obtained in accordance with the invention by a general method A if arylisocyanates of general formula III

Q—N═C═O III in which $R^4$ to $R^{17}$ have the meanings; indicated above, and proline carboxylic acids (esters) of general formula IV

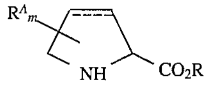

IV in which m and $R^A$ have the meaning Indicated above and R═H or $(C_1-C_4)$alkyl or active ester such as 0-succimid esters or anhydride esters are reacted in accordance with method A, optionally in the presence of an acid acceptor and optionally in the presence of a solvent.

A further subject of the invention is a method B for the preparation of compounds of formula I, which is outlined in what follows and m and $R^A$ have the meanings indicated above. Therefor a compound of formula IV, wherein R═H or $(C_1-C_4)$alkyl, is reacted with phosgene or a phosgene substituted [e.g., triphosgene $(CCl_3O)_2C$═O], first to compounds of formula V. Compounds of formula V are then reacted with compounds of formula VI to form compounds of formula VII. Subsequent cyclization forms compounds formula I.

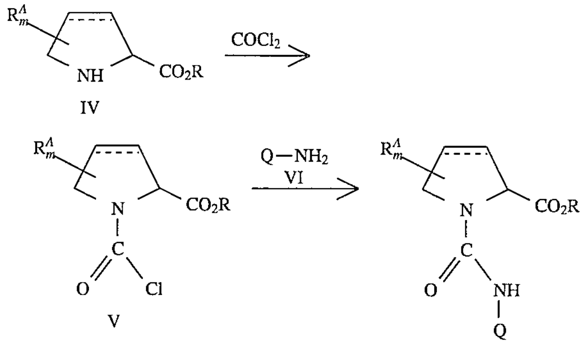

IV V VII

A further subject of the invention is method C for the preparation of compounds of formula I, which is outlined in what follows and m and $R^A$ have the meanings indicated above, where a compound of formula III is reacted with a compound of formula VIII, optionally in the presence of an acid acceptor and optionally in the presence of a solvent, to a compound of formula IX, and the compound IX so obtained is then hydrolysed and cyclized to compounds of formula I.

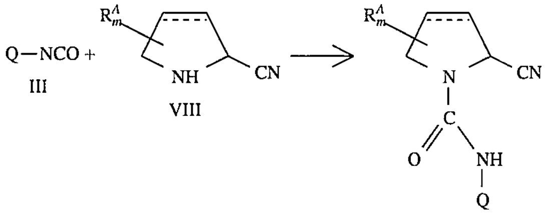

III VIII IX

A further subject of the invention is method D for the preparation of compounds of formula II, which is outlined in what follows and $R^1$ and $R^2$ have the meaning indicated above. Therefor a compound of general formula X, wherein R=H or $(C_1-C_4)$alkyl, is reacted with a compound of general formula III, yielding a compound of general formula XI. Compounds of general formula XI are cyclized to compounds of general formula XII and converted to compounds of formula II.

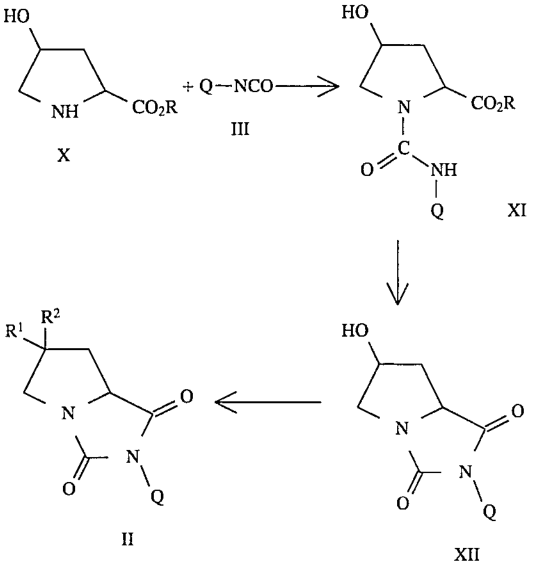

X III XI II XII

A further subject of the invention is a method E for the preparation of compounds of formula I by reacting compounds of general formula XIII

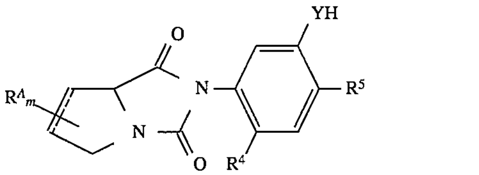

XIII wherein m, $R^A$, and $R^5$ have the meaning indicated above and Y=0, S, NH with a halide of the formula XIV, XV or XVI, $R^{10}$—Z XIV $R^{15}SO_2$—Z XV $R^{15}NHSO_2$—Z XVI wherein Z is a chlorine-, bromine—or an iodine atom and $R^{10}$ and $R^{15}$ have the meanings indicated above.

In method A, the reaction for R=alkyl takes place in an inert organic solvent, for example in an aromatic solvent such as toluene, chlorobenzene, a halogenated hydrocarbon such as chloroform, methylene chloride, an ether such as diisopropyl ether, or in acetonitrile or dimethylformamide, optionally with base catalysis preferred at temperatures of 20° to 120° C. Preferably used as bases are organic bases, for example organic amines such as triethylamine or also pyridine (see EP-A 0 272 594).

For R=H, the reaction takes place in water as solvent or, preferably, in the two-phase system water organic solvent. Especially preferred is the mode of operation in which compounds of formula IV, optionally salts of IV, is added together in water with an inorganic base, for example an alkali or alkaline-earth metal hydroxide, carbonate or hydrogen carbonate, such as sodium hydroxide or also potassium carbonate, or an organic base, for example an organic amine such as triethylamine, and then compounds of formula III, dissolved in an inert solvent such as, for example toluene, chlorobenzene or chloroform is added. The reaction mixture is then held advantageously at temperatures between –40° C. to +120° C. preferably –10° C. to +40° C., up to several days, preferably between 3 and 50 h.

The aqueous phase is then adjusted to a pH value between 1 and 3 with acid, preferably with an inorganic acid such as aqueous hydrochloric acid or aqueous sulfuric acid. The ureas of formula VII thus formed are then cyclized at temperatures between 50° and 100° C. or, optionally, in the presence of an acid such as hydrochloric acid and/or hydroformic acid or, optionally by conversion to an ester (R=alkyl) by know methods (see Houben-Weyl, "Methoden der organischen Chemie" [Methods of Organic Chemistry], Vol. XV (1974)).

In method D, the reaction for R=H and $(C_1-C_4)$alkyl takes place analogous to method A to give compounds formula XII. Known methods (see Houben-Weyl, "Methoden der organischen Chemie" [Methods of Organic Chemistry] Vol. EP-B 0 078 191) and standard chemistry (see Advanced Organic Chemistry, Jerry March, second edition 1977) leads to compounds of formula II.

The compounds of formula III are known or can be prepared by analogy with known methods; see Houben-Weyl, "Methoden der organisthen Chemie" [Methods of Organic Chemistry], Vol. VIII, p. 120 (1952), Houben-Weyl, Vol. IX, pp. 875, 869 (1955); EP-B 0 070 389 US-A 4 881 967; EP-A 0 322 401; US-A 3 495 967; EP-A 0 300 307; EP-A 0 349 832.

Compounds of general formula IV or X are commercially available or prepared according to methods described in the literature (e.g. S. Kanenasa et al., J. Org. Chem. 56, 2875 (1991); P. Beaulien et al., J. Chem. Soc. Perkin. Trans. I 11, 2885 (1991): R. M. Kellog et al., Tetrahedron Lett. 32(30), 3727 (1991) and many more). Houben-Weyl. Vol. XXV/1 and XXV/2 (1974). The latter literature describes also the active esters.

Amines of general formula VIII are known or can be prepared in accordance with EP-A 0 073 569 or in an analogous fashion in accordance witch the method described there.

The 2R-configuration can be achieved starting from the corresponding optically active proline or proline derivatives analogous to the methods specified above.

Finally, it was found that the bicyclic imides of general formula I and II exhibit outstanding herbicidal qualities.

A further subject of the invention is a composition for controlling weeds comprising an effective amount of at least one of the novel bicyclic imides and at least one carrier therefor.

A further subject of the invention is a method for controlling weeds comprising applying to the locus to be protected an effective amount of at least one of the novel bicyclic imides.

A further subject of the invention is a method for controlling weeds in plantation crops and peanut comprising applying to the locus to be protected an effective amount of a compound of formula Ia:

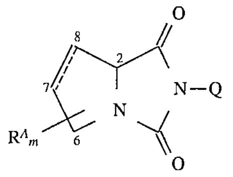

Ia wherein the bond linking C-7 and C-8 may be single or double;

m is 1–7;

$R^A$ can occupy one or more of the 2 or 6–8 positions and is independently selected from the group: hydroxy, halogen, CN, $OR^3$, $(C_1–C_4)$alkyl, $S(O)_nR^3$, $COR^3$, $C(O)SR^3$, and $C(O)NR^{11}R^{12}$;

Q is

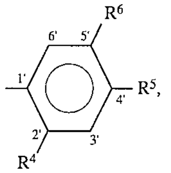

Q-1

Q-1

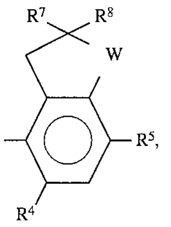

Q-2

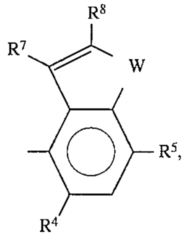

Q-3

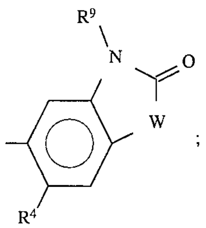

Q-4

;

-continued

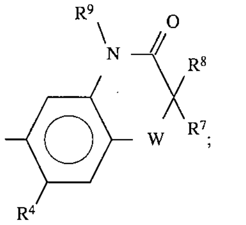

Q-5

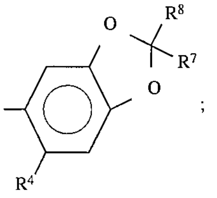

Q-6

;

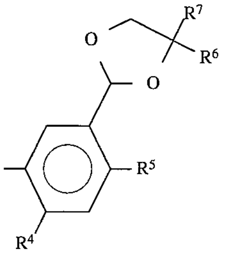

Q-7 wherein $R^3$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_4)$carboxy alkyl, $(C_3–C_8)$alkoxycarbonylalkyl, $(C_4–C_8)$alkenyloxyalkyl, $(C_4–C_8)$alkynyloxyalkyl, $(C_3–C_8)$haloalkoxyalkyl, $(C_3–C_8)$trialkylsilyl, $(C_3–C_8)$cyanoalkyl, $(C_3–C_8)$haloalkenyl, $(C_3–C_8)$haloalkynyl, $(C_2–C_8)$alkylcarbonyl, $(C_2–C_8)$alkoxycarbonyl, $(C_2–C_8)$haloalkoxycarbonyl, $P(O)(OR^{17})_2$, $CHR^{16}P(O)(OR^{17})_2$ or $CHR^{16}P(S)(OR^{17})_2$, phenyl or benzyl optionally substituted with halogen, $(C_1–C_3)$alkyl, $(C_1–C_3)$haloalkyl or $(C_1–C_4)$alkoxy;

$R^4$ is hydrogen or halogen;

$R^5$ is $(C_1–C_2)$alkyl, $(C_1–C_2)$haloalkyl, $OCH_3$, $SCH_3$, $OCHF_2$, halogen, CN or $NO_2$;

$R^6$ is hydrogen, $(C_1–C_8)$alkyl, $(C_1–C_8)$haloalkyl, halogen, $OR^{10}$, $S(O)_nR^{10}$, $COR^{10}$, $C(O)SR^{10}$, $C(O)NR^{11}R^{12}$, CHO, $CH{=}CHCO_2R^{10}$, $CO_2N{=}CR^{13}R^{14}$, $NO_2$, CN, $NHSO_2R^{15}$ or $NHSO_2NHR^{15}$;

$R^7$ and $R^8$ are independently hydrogen, $(C_1–C_3)$alkyl, $(C_1–C_3)$haloalkyl or halogen; when Q is Q-2 or Q-6, $R^7$ and $R^8$ together with the carbon to which they are attached may be C=O;

$R^9$ is $(C_1–C_6)$alkyl, $(C_1–C_6)$haloalkyl, $(C_2–C_6)$alkoxyalkyl, $(C_3–C_6)$alkenyl or $(C_3–C_6)$alkynyl;

$R^{10}$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$alkoxyalkyl, $(C_2–C_6)$alkylthioalkyl, $(C_2–C_8)$alkylsulfinylalkyl, $(C_2–C_8)$alkylsulfonylalkyl, $(C_3–C_8)$alkoxyalkoxyalkyl, $(C_1–C_8)$cycloalkylalkyl, $(C_2–C_4)$carboxyalkyl, $(C_3–C_8)$alkoxycarbonylalkyl, $(C_6–C_8)$alkenyloxycarbonylalkyl, $(C_6–C_8)$alkynyloxycarbonylalkyl, $(C_6-C_8)$cycloalkoxyalkyl, $(C_1-C_8)$alkenyloxyalkyl, $(C_4-C_8)$alkynyloxyalkyl, $(C_3-C_8)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_3-C_8)$cyanoalkyl, $(C_3-C_8)$halocycloalkyl, $(C_3-C_8)$haloalkenyl, $(C_5-C_8)$alkoxyalkenyl, $(C_5-C_8)$haloalkoxyalkenyl, $(C_5-C_8)$alkylthioalkenyl, $(C_3-C_8)$haloalkynyl, $(C_5-C_8)$alkoxyalkynyl, $(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)NR^{11}IR^{12}$, $CHR^{16}C(O)NH_2$, $(C_1-C_4)$alkyl substituted with phenoxy or benzyloxy optionally substituted with halogen, $(C_1-C_3)$alkyl or $(C_1-C_3)$haloalkyl; benzyl optionally substituted with halogen, $(C_1-C_3)$alkyl or $(C_1-C_3)$haloalkyl; or phenyl and pyridyl optionally substituted with halogen, $(C_1-C_3)$alkyl, $(C_1-C_3)$haloalkyl or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, or phenyl optionally substituted with halogen, $(C_1-C_3)$alkyl, $(C_1-C_3)$haloalkyl or $(C_1-C_4)$alkoxy;

$R^{11}$ and $R^{12}$ may be taken together as $—(CH_2)_5—$, $—(CH_2)_4—$ or $—CH_2CH_2OCH_2CH_2—$, in which optionally one or more H-atoms may be replaced by $(C_1-C_3)$alkyl, phenyl or benzyl;

$R^{13}$ and $R^{14}$ may be taken together with the carbon to which they are attached to form $(C_3-C_8)$cycloalkyl;

$R^{15}$ is $(C_1-C_4)$alkyl or $(C_1-C_4)$haloalkyl;

$R^{16}$ is hydrogen or $(C_1-C_3)$alkyl;

$R^{17}$ is $(C_1-C_6)$alkyl; $(C_3-C_6)$alkenyl or $(C_3-C_6)$alkynyl;

W is 0 or S;

n is 0, 1, or 2.

In this method is preferred the plantation crop selected from the group consisting of citrus, sugarcane, coffee, banana, oil palm, grapes and rubber. Further is preferred employing at least one of the compounds of the group consisting of 4-[4'-chloro-2'-fluoro-5'-(1-methylethoxy)phenyl]-3,5-dioxo-7-fluoro-1,4-diazabicyclo[3.3.0]octane, 4-[4'-chloro-2'-fluoro-5'-(1-methyl-prop-2-ynyloxy)phenyl]-3,5-dioxo-7-fluoro-1,4-diazabicyclo[3.3.0]octane, 4-[4'-chloro-2'-fluoro-5'-(prop-2-ynyloxy)phenyl]-3,5-dioxo-7-fluoro-1,4-diazabicyclo[3.3.0]octane, 4-[4'-chloro-2'-fluoro-5'-(1-methyl-ethoxy)phenyl]-3,5-dioxo-7,7-difluoro-1,4-diazabicyclo[3.3.0]octane, 2-(7-fluoro-3-oxo-4-prom-2-ynyl-3,4-dihydro-2H-benzo[1,4]oxazin-6-yl)-tetrahydropyrrolo[1,2c]imidazole-1,3-dione, 6,6-difluoro-2-(7-fluoro-3-oxo-4-prop-2-ynyl-3,4-dihydro-2H-benzo[1.4]oxazin-6-yl)tetrahydropyrrolo[1,2-c]imidazole-1,3-dione (JUPAC), 4-[2-chloro-4-fluoro-5-(6-fluoro-1,3-dioxotetrahydropyrrolo[1,2-c]imidazol-2-yl)phenoxy]but-2-enoic acid methyl ester (JUPAC) and stereoisomers thereof. Preferred is also a method in which the crop is peanut and the compound is applied preemergence.

Chemical examples

EXAMPLE 1

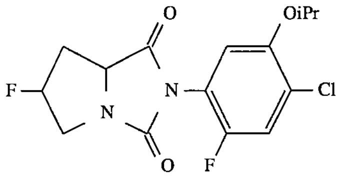

A mixture of 2(R)-Carbomethoxy-4-fluoropyrrolidine (1,47 g, 0,01 ml), triethylamine (50,0 mg, 0,5 mmol) and toluene (30 ml) is prepared, and 4-chloro-2-fluoro-5-isopropoxyphenyl isocyanate (2,29 g, 0,01 mol) dissolved in toluene (20 ml) is added dropwise. The reaction mixture is stirred for 5 h at reflux, then washed with 10% aqueous hydrochloric acid (3×10 ml) and water (3×10 ml), dried over sodium sulfate, and filtered. After concentration of the filtrate by evaporation, the resulting residue is purified by silica gel chromatography.

2R-4-(4'-Chloro-2 -fluoro-5'-isopropoxyphenyl)-3,5-dioxo-7-fluoro-1,4-diazabicyclo[3.3.0]octane is obtained in the amount of 2.58 g (75% theoretical) as colourless crystals (m.p. 103°–105° C.).

EXAMPLE 2

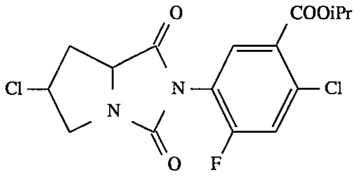

2R-4-(4'-chloro-2'-fluoro-5'-carboisopropoxy)-3,5-dioxo-7-hydroxy-1,4-diazabicyclo[3.3.0]octane 3.71 g (0.01 mol) is dissolved in toluene (30 ml) and cooled to 0°–5° C., before thionyl chloride (1.44 g, 12.0 mmol) in toluene (10 ml) is added dropwise. The reaction mixture is refluxed for 15 h. The solvent and the excess of thionyl chloride is evaporated and the residue is purified by silica gel chromatography, 2R-4-(4'-chloro-2'-fluoro-5'-carboisopropoxy)-7-chloro-3,5-dioxo-1,4-diazabicyclo[3.3.0] octane is obtained in the amount of 3,19 g (82% of theoretical) as a colorless glass.

EXAMPLE 3

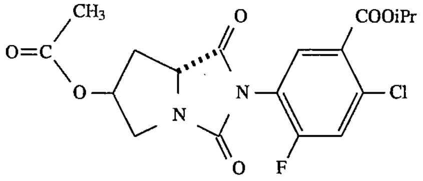

A mixture or 2R-4-(4-chloro-2-fluoro-5'-carboisopropoxyphenyl)-3,5-dioxo-7-hydroxy-1,4-diazabicyclo[3.3.0] octane (3.71 g, 0,01 mol), triethylamine (1,41 g. 14.0 mol) and acetic acid anhydride (1.24 g, 12.0 mmol) are added together in methylene chloride (30 ml) and toluene (60 ml). The reaction mixture is refluxed for 13 h. cooled to room temperature and the organic layer is washed with water (3×15 ml). The collected organic layers are dried over sodium sulfate, and filtered. After concentration of the filtrate by evaporation, the resulting residue is purified by silica gel chromatography.

2R-4-(4'-Chloro-2 -fluoro-.5 -isopropoxyphenyl)-3,5-dioxo-7-methylcarbonyloxy-1,4-diazabicyclo[3.3.0]octane is obtained in the amount of 2.84 g (69% of theoretical) as a colourless glass.

EXAMPLE 4

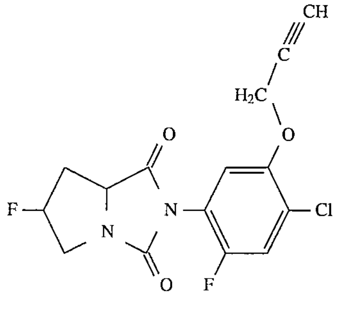

A mixture of 4-(4-(4-Chloro-2'-fluoro-5 -hydroxyphenyl)-3,5-dioxo-7-fluoro-1,4-diazabicyclo[3.3.0]octane (3,03 g, 0.01 mol), potassium carbonate (6.95 g, 0,05 mol) propargyl bromide (1,78 g, 12.0 mmol) and acetonitrile (60 ml) is stirred for 20 h at 20° C. The reaction mixture is acidified to pH=2 with 5% aqueous hydrochloric acid, followed by extraction with ether (3x15 ml). The ether layer is dried over sodium sulfate, and filtered. After evaporation of the solvent, the residue is purified by silica gel chromatography.

4-(4'-Chloro-2-fluoro-5-propargyloxyphenyl)-3,5-dioxo-7-fluoro-1,4-diazabicyclo[3.3.0] octane is obtained in the amount of 3,16 g (93% of theoretical) in two fractions as, two diastereomers (or diastereomeric mixtures).

1. Fraction: m.p. 136°–139° C. $[\alpha]_D^{20}$=+45.1° C.

2. Fraction: m.p. 143°–145° C. $[\alpha]_D^{20}$=–35.2° C.

Analogously to Example 1 to 4 and in accordance with the general discription of the methods A to E in accordance with the invention, the compounds of general formula I lasted in the following tables can be prepared:

TABLE 1

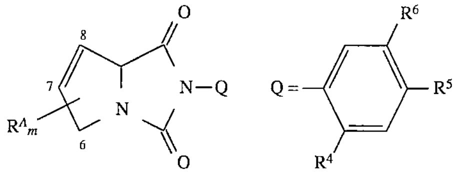

| $R^A$ | $R^4$ | $R^5$ | $R^6$ | melting point °C. |
|---|---|---|---|---|
| H | 7-F | Cl | H | |
| H | 8-F | Cl | H | |
| H | 7-Cl | Cl | $CO_2CH(CH_3)_2$ | |
| H | 8-Cl | Cl | $OCH(CH_3)_2$ | |
| H | 6-F | Cl | $OCH_2C\equiv CH$ | |
| H | 7-Br | Cl | $OCH(CH_3)C\equiv CH$ | |

TABLE 2

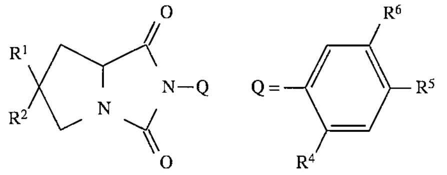

| $R^1$ | $R^2$ | $R^4$ | $R^5$ | $R^6$ | melting point °C. |
|---|---|---|---|---|---|
| F | H | H | Cl | H | |
| F | H | H | Br | H | |
| F | H | H | $CH_3$ | H | |
| F | H | F | Cl | H | |
| F | H | Cl | Cl | H | |
| F | H | F | Cl | $OCH(CH_3)_2$ | 91–93 (R/S-Mixture at Pos. 2 and 7) |
| F | H | F | Cl | $OCH(CH_3)_2$ | 103–105 (2R, 7S-Konfiguration, $[\alpha]_D^{20}$ = +48,8 (c = 0,5 in $CH_2Cl_2$)) |
| F | H | F | Cl | $OCH(CH_3)_2$ | glass (2R, 7R-Konfiguration, $[E]_D^{20}$ = +38,3 (c = 1 in $CH_3OH$)) |
| F | H | F | Cl | $OCH(CH_3)_2$ | glass |
| F | H | F | Cl | $OCH_2C\equiv CH$ | 143–145 (2S, 7R/S-Konfiguration, $[\alpha]_D^{20}$ = –35,2 (c = 0,5 in $CH_3OH$)) |
| F | H | F | Cl | $OCH_2C\equiv CH$ | 136–139 (2R, 7R/S-Konfiguration, $[\alpha]_D^{20}$ = +45,1 (c = 0,5 in $CH_2OH$)) |
| F | H | F | Cl | $OCH_2C\equiv CH$ | glass (2R/S, 7R/S-Konfiguration) |
| F | H | F | Cl | $OCH(CH_3)C\equiv CH$ | 133–139 (2S, 7R/S-Konfiguration, $[\alpha]_D^{20}$ = –29,9 |

TABLE 2-continued

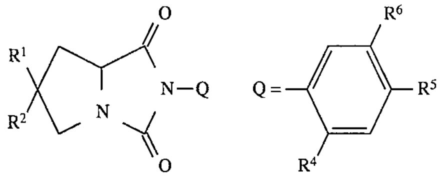

| $R^1$ | $R^2$ | $R^4$ | $R^5$ | $R^6$ | melting point °C. |
|---|---|---|---|---|---|
| | | | | | (c = 0,5 in $CH_3OH$)) |
| F | H | F | Cl | $OCH(CH_3)C{\equiv}CH$ | 121–124 (2R, 7R/S-Konfiguration, $[\alpha]_D^{20}$ = +41,5 (c = 0,5 in $CH_3OH$)) |
| F | H | F | Cl | $OCH(CH_3)C{\equiv}CH$ | glass (2R/S, 7R/S-Konfiguration) |
| F | H | F | Cl | $OCH_3$ | |
| F | H | F | Cl | $OCH_2CH_2CH_3$ | |
| F | H | F | Cl | $OCH_2CH{=}CH_2$ | |
| F | H | F | Cl | $OCH_2CH{=}CHCO_2CH_3$ | glass |
| F | H | F | Cl | $OCH_2CO_2CH_3$ | |
| F | H | F | Cl | $OCH_2CO_2CH_2C{\equiv}CH$ | |
| F | H | F | Cl | $OCH_2CO_2C_5H_{11}$ | |
| F | H | F | Cl | CN | |
| F | H | F | Cl | $SCH_3$ | |
| F | H | F | Cl | $SCH(CH_3)_2$ | |
| F | H | F | Cl | $SCH_2CH{=}CH_2$ | |
| F | H | F | Cl | $SCH_2C{\equiv}CH$ | |
| F | H | F | Cl | $SCH_2CO_2H$ | |
| F | H | F | Cl | $SCH_2CO_2CH_3$ | |
| F | H | F | Cl | 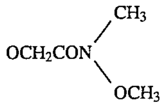 | |
| F | H | F | Cl | $OC(CH_3){=}N{-}OCH_3$ | |
| F | H | F | Cl | $SCH_2CO_2CH_2C{\equiv}CH$ | |
| F | H | F | Cl | $OCHF_2$ | |
| F | H | F | Cl | $OCH_2C(Cl){=}CH_2$ | |
| F | H | F | Cl | $OCF_2CHFCl$ | |
| F | H | F | Cl | $NHSO_2CH_3$ | |
| F | H | F | Cl | $NHSO_2CH(CH_3)_2$ | |
| F | H | F | Cl | $NHSO_2NHCH_3$ | |
| F | H | F | Cl | $CO_2CH(CH_3)_2$ | oil (2R, 7R/S-Konfiguration, $[\alpha]_D^{20}$ = +32,4 (c = 0,5 in $CH_2Cl_2$)) |
| F | H | F | Cl | $CO_2CH_2CH_2CH_3$ | |
| F | H | F | Cl | $CO_2CH_2CF_3$ | |
| F | H | F | Cl | $CO_2CH(CH_3)_2$ | oil (2R/S, 7R/S-Konfiguration) |
| F | H | F | Cl | $CO_2N(CH_3)_2$ | |
| F | H | F | Cl | $CO_2CH(CH_3)CH_2CH_3$ | |
| F | H | F | Cl | $CO_2CH(CH_3)CF_3$ | |
| F | H | F | Cl | 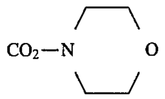 | |
| F | H | F | Cl | $CO_2CH(CH_3)CH_2SCH_3$ | |
| Cl | H | F | Cl | H | |
| Cl | H | F | Cl | $OCHF_2$ | |
| Cl | H | F | Cl | $OCH(CH_3)_2$ | oil (2R, 7S-Konfiguration, $[\alpha]_D^{20}$ = +41,7 (c = 0,5 in $CH_2Cl_2$)) |
| Cl | H | F | Cl | $OCF_2CHFCl$ | |
| Cl | H | F | Cl | $OCH_2C{\equiv}CH$ | oil (2R, 7S-Konfiguration, $[\alpha]_D^{20}$ = −35,8 (c = 0,5 in $CH_3OH$)) |

TABLE 2-continued

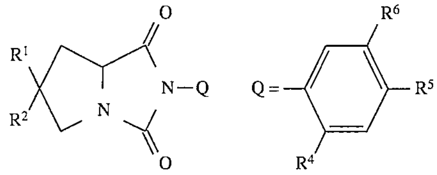

| $R^1$ | $R^2$ | $R^4$ | $R^5$ | $R^6$ | melting point °C. |
|---|---|---|---|---|---|
| Cl | H | F | Cl | $OCH_2C{\equiv}CH$ | glass (2R, 7S-Konfi-guration) |
| Cl | H | F | Cl | $OCH_2C{\equiv}CH$ | glass (2R/S, 7S-Konfi-guration) |
| Cl | H | F | Cl | $OCH_2P(O)(C_2H_5)_2$ | |
| Cl | H | F | Cl | $OCH(CH_3)C{\equiv}CH$ | oil (2R, 7S-Konfi-guration) |
| Cl | H | F | Cl | $OCH(CH_3)C{\equiv}CH$ | 130–145 (2S, 7S-Konfi-guration, $[\alpha]_D^{20}$ = −27,3 in $CH_3OH$)) |
| Cl | H | F | Cl | $OCH_2C(O)N(CH_3)_2$ | |
| Cl | H | F | Cl | $O(CH_2)_2OCH_2CH_3$ | |
| Cl | H | F | Cl | $OCH_2CH{=}N{-}OCH_2CH{=}CH_2$ | |
| Cl | H | F | Cl | $SCH_2C{\equiv}CH$ | |
| Cl | H | F | Cl | $SCH_2CO_2H$ | |
| Cl | H | F | Cl | $SCH_2CO_2CH_2C{\equiv}CH$ | |
| Cl | H | F | Cl | $NHSO_2CH_3$ | |
| Cl | H | F | Cl | $NHSO_2CF_3$ | |
| Cl | H | F | Cl | $CO_2CH(CH_3)_2$ | oil (2R, 7S-Konfi-guration, $[\alpha]_D^{20}$ = +36,6 (c = 0,5 in $CH_2Cl$)) |
| Cl | H | F | Cl | $CO_2CH(CH_3)CH_2SCH_3$ | |
| Cl | H | F | Cl | $CO_2CH(CH_3)CF_3$ | |
| Cl | H | F | Cl | $CO_2N(CH_3)_2$ | |
| Cl | H | F | Cl | $CO_2CH_2C{\equiv}CH$ | |
| Cl | H | F | Cl | $CO_2CH(CH_3)C{\equiv}CH$ | |
| Cl | H | F | Cl | $CO_2CH_2CF_3$ | |
| Cl | H | F | Cl | 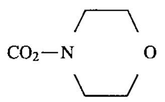 | |
| Cl | H | F | Cl | $CO_2(CH_2)_2CH_3$ | oil (2R, 7S-Konfi-guration) |
| Cl | H | F | Cl | $CH{=}CHCO_2CH_2CH_3$ | |
| $OSi(CH_3)_3$ | H | F | Cl | $CO_2CH(CH_3)_2$ | oil (2R, 7S-Konfi-guration, $[\alpha]_D^{20}$ = +29,5 (c = 0,5 in $CH_2Cl_2$)) |
| $OSi(CH_3)_3$ | H | F | Cl | $OCH_2C{\equiv}CH$ | |
| $OSi(CH_3)_3$ | H | F | Cl | $OCH(CH_3)C{\equiv}CH$ | |
| $OC(O)CH_3$ | H | F | Cl | $CO_2CH(CH_3)_2$ | oil (2R, 7S-Konfi-guration) |
| $OC(O)CH_3$ | H | F | Cl | $CO_2CH(CH_3)_2$ | oil (2R, 7R-Konfi-guration) |
| $OC(O)CH_3$ | H | F | Cl | $OCH_2C{\equiv}CH$ | |
| $OCO_2CH_3$ | H | F | Cl | $OCH(CH_3)_2$ | oil (2R, 7S-Konfi-guration) |
| $OCO_2CH_3$ | H | F | Cl | $OCH(CH_3)_2$ | oil (2R, 7R-Konfi-guration) |
| $OSO_2CH_3$ | H | F | Cl | $OCH(CH_3)_2$ | 140–141 (2R, 7R-Konfi-guration, $[\alpha]_D^{20}$ = +56,3 in $CH_2Cl_2$)) |
| $OCH_3$ | H | F | Cl | $CO_2CH(CH_3)_2$ | oil (2R, 7R-Konfi-guration, $[\alpha]_D^{20}$ = +55,1 (c = 0,5 in $CH_2Cl_2$)) |
| $OCH_3$ | H | F | Cl | $CO_2CH_2CH_2CH_3$ | |
| $OCH_3$ | H | F | Cl | $OCH(CH_3)_2$ | |

TABLE 2-continued

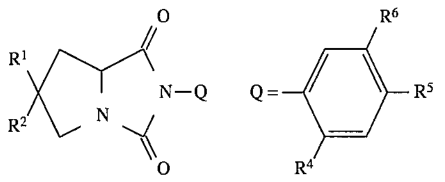

| $R^1$ | $R^2$ | $R^4$ | $R^5$ | $R^6$ | melting point °C. |
|---|---|---|---|---|---|
| $OCH_3$ | H | F | Cl | $OCH_2C{\equiv}CH$ | |
| OH | H | F | Cl | $OCH(CH_3)_2$ | 63–65 (2R, 7R/S-Konfiguration, $[\alpha]_D^{20}$ = +47,1 (c = 0,5 in $CH_3OH$)) |
| OH | H | F | Cl | $CO_2CH(CH_3)_2$ | 45–48 (2S/7R/S-Konfiguration) |
| OH | H | H | Cl | H | 161,5–63 |
| OH | H | F | Cl | $CO_2CH(CH_3)_2$ | 110–112 (2R/7R-Konfiguration, $[\alpha]_D^{20}$ = +39,2 (c = 0,5 in $CH_3OH$) |
| $OCH_3$ | H | F | Cl | $OCH(CH_3)C{\equiv}CH$ | |
| $OCH_2C{\equiv}CH$ | H | F | Cl | $CO_2CH(CH_3)_2$ | |
| $CH_3$ | H | F | Cl | $CO_2CH(CH_3)_2$ | |
| $CO_2H$ | H | F | Cl | $OCH(CH_3)_2$ | |
| $CO_2H$ | H | F | Cl | $CO_2CH(CH_3)_2$ | |
| Br | H | F | Cl | $CO_2CH(CH_3)_2$ | |
| Br | H | F | Cl | $CO_2CH(CH_3)CH_2CH_3$ | |
| Br | H | F | Cl | $OCHF_2$ | |
| Br | H | F | Cl | $OCH(CH_3)_2$ | oil (2R, 7S-Konfiguration, $[\alpha]_D^{20}$ = +26,5 (c = 0,5 in $CH_2Cl_2$) |
| Br | H | F | Cl | $OCF_2CHF_2$ | |
| Br | H | F | Cl | $OCH_2C{\equiv}CH$ | |
| Br | H | F | Cl | $OCH(CH_3)C{\equiv}CH$ | |
| Br | H | F | Cl | $SCH_2CO_2H$ | |
| Br | H | F | Cl | $NHSO_2CH_3$ | |
| Br | H | F | Cl | $NHSO_2CF_3$ | |
| F | F | F | Cl | $OCH(CH_3)_2$ | 99–101 (2R-Konfiguration, $[\alpha]_D^{20}$ = −34,2 (c = 0,5 in $CHCl_3$)) |
| F | F | F | Cl | $OCH_2CH{=}CH_2$ | glass |
| F | F | F | Cl | $OCF_2CH{=}CH_2$ | glass |
| F | F | F | Cl | $CO_2CH(CH_3)_2$ | |
| F | F | F | Cl | $SCH_2CO_2CH_3$ | |
| F | F | F | Cl | $OCH_2C{\equiv}CH$ | |
| F | F | F | Cl | $OCH(CH_3)C{\equiv}CH$ | |
| F | F | Cl | Cl | $CO_2CH(CH_3)_2$ | |
| F | F | Cl | Cl | $OCH_2C{\equiv}CH$ | |
| F | F | Cl | Cl | $OCH(CH_3)C{\equiv}CH$ | |

TABLE 3

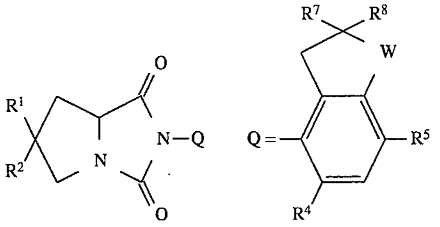

| $R^1$ | $R^2$ | $R^4$ | $R^5$ | $R^7$ | $R^8$ | w | melting point °C. |
|---|---|---|---|---|---|---|---|
| F | H | F | Cl | H | $CH_2$ | O | glass (2R/S, 7S-Konfiguration) |

TABLE 3-continued

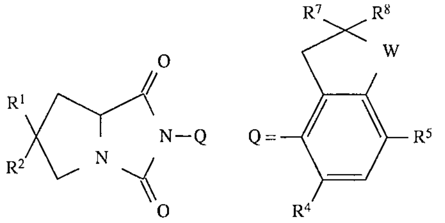

| $R^1$ | $R^2$ | $R^4$ | $R^5$ | $R^7$ | $R^8$ | w | melting point °C. |
|---|---|---|---|---|---|---|---|
| F | H | F | Cl | H | $CH_3$ | O | glass (2S, 7S-Konfiguration, $[\alpha]_D^{20}$ = +19,5 (c = 0,5 in $CH_2Cl_2$)) |
| F | H | F | Cl | H | $CH_3$ | O | glass (2R, 7S-Konfiguration, $[\alpha]_D^{20}$ = −16,6 (c = 0,5 in $CH_2Cl_2$) |
| F | H | F | Cl | H | H | O | |
| F | H | F | Cl | $CH_3$ | $CH_3$ | O | |
| F | H | F | Cl | $CH_3$ | $CH_2F$ | O | |
| F | H | F | Cl | H | $CH_2CH_3$ | O | |
| F | H | F | Cl | H | $CH_2F$ | O | |
| F | H | F | Cl | H | $CH_2Cl$ | O | |
| F | H | F | Cl | H | $CH_2Br$ | O | |
| F | H | F | Br | H | $CH_3$ | O | |
| F | H | F | $CH_3$ | H | $CH_3$ | O | |
| F | H | F | $OCH_3$ | H | $CH_3$ | O | |
| F | H | F | CN | H | $CH_3$ | O | |
| F | H | F | $CF_3$ | H | $CH_3$ | O | |
| F | F | F | Cl | H | $CH_3$ | O | 151-154 |
| F | F | Cl | Cl | H | $CH_3$ | O | |
| F | H | F | $OCF_2H$ | H | $CH_3$ | O | |
| F | H | Cl | Cl | H | $CH_3$ | O | |
| Cl | H | F | Cl | H | $CH_3$ | O | |
| Cl | H | Cl | Cl | H | $CH_3$ | O | |
| Cl | H | F | Cl | $CH_3$ | $CH_3$ | O | |
| Cl | H | F | Cl | $CH_3$ | $CH_2F$ | O | |
| Cl | H | F | Cl | H | $CH_2F$ | O | |
| Cl | H | F | Cl | H | $CH_2Cl$ | O | |
| Cl | H | F | Cl | H | $CH_2Br$ | O | |
| Cl | H | F | Cl | H | $CH(CH_3)_2$ | O | |
| Cl | H | F | Cl | H | $CH_2CH_2Cl$ | O | |
| Cl | H | F | Cl | H | $CH_2CH_3$ | O | |
| Cl | H | F | Cl | H | $CH_2(CH_2)_2F$ | O | |
| Cl | H | F | Br | H | $CH_3$ | O | |
| Cl | H | F | $CH_3$ | H | $CH_3$ | O | |
| Cl | H | F | $OCH_3$ | H | $CH_3$ | O | |
| Cl | H | F | CN | H | $CH_3$ | O | |
| Cl | H | F | $CF_3$ | H | $CH_3$ | O | |
| Cl | H | F | $OCF_2H$ | H | $CH_3$ | O | |
| $OCH_3$ | H | F | Cl | H | $CH_3$ | O | |
| $OSi(CH_3)_3$ | H | F | Cl | H | $CH_3$ | O | |
| $CH_3$ | H | F | Cl | H | $CH_3$ | O | |
| $CO_2H$ | H | F | Cl | H | $CH_3$ | O | |
| Br | H | F | Cl | H | $CH_3$ | O | |
| Br | H | F | Cl | H | $CH_2F$ | O | |
| Br | H | F | Cl | H | $CH_2Br$ | O | |
| Br | H | F | Cl | $CH_3$ | $CH_3$ | O | |
| Br | H | F | Cl | $CH_3$ | $CH_2F$ | O | |
| Br | H | Cl | Cl | H | $CH_3$ | O | |

TABLE 4

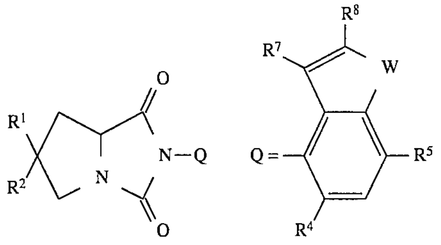

| $R^1$ | $R^2$ | $R^4$ | $R^5$ | $R^7$ | $R^8$ | w | melting point °C. |
|---|---|---|---|---|---|---|---|
| F | H | F | Cl | H | Cl | S | |
| F | H | F | Cl | H | $CH_3$ | S | |
| F | H | F | Cl | H | $CH_2CH_3$ | S | |
| F | H | H | $SCH_3$ | H | H | S | |
| F | H | F | Cl | H | Cl | O | |
| F | H | F | Cl | H | $CH_3$ | O | |
| Cl | H | F | Cl | H | Cl | S | |
| Cl | H | F | Cl | H | $CH_3$ | S | |
| Cl | H | F | Cl | H | $CH_2CH_3$ | S | |
| Cl | H | H | $SCH_3$ | H | H | S | |
| Cl | H | F | Cl | H | Cl | O | |
| Cl | H | F | Cl | H | $CH_3$ | O | |
| $OCH_3$ | H | F | Cl | H | $CH_3$ | S | |
| $OCH_3$ | H | F | Cl | H | Cl | S | |
| Br | H | F | Cl | H | $CH_3$ | S | |
| F | F | F | Cl | H | Cl | S | |
| Br | H | F | Cl | H | Cl | S | |
| Br | H | F | Cl | H | $CH_3$ | O | |
| $OSi(CH_3)_3$ | H | F | Cl | H | $CH_3$ | S | |

TABLE 5

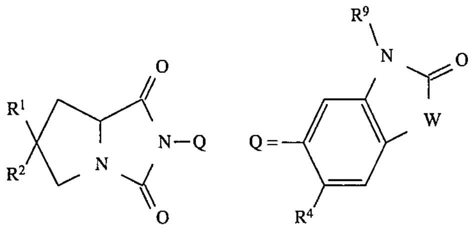

| $R^1$ | $R^2$ | $R^4$ | $R^9$ | w | melting point °C. |
|---|---|---|---|---|---|
| H | H | F | $CH_2C{\equiv}CH$ | O | |
| F | H | F | H | S | |
| F | H | F | $CH_3$ | S | |
| F | H | F | $CH_2CH_3$ | S | |
| F | H | F | $CH_2C{\equiv}CH$ | S | |

TABLE 5-continued

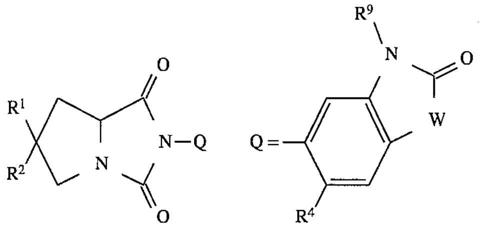

| $R^1$ | $R^2$ | $R^4$ | $R^9$ | w | melting point °C. |
|---|---|---|---|---|---|
| F | H | F | $CH_2CH{=}CH_2$ | S | |
| F | H | F | $CH_2OCH_2$ | S | |
| F | H | F | $CH_2CH_2CH_3$ | S | |
| F | H | F | $CH(CH_3)C{\equiv}CH$ | S | |
| F | H | F | $CH(CH_3)_2$ | S | |
| F | H | F | $CF_2CHF_2$ | S | |
| F | F | F | $CH_2C{\equiv}CH$ | S | |
| F | F | F | $CH_2CH{=}CH_2$ | S | |
| F | F | F | $CH_2CO_2CH_3$ | S | |
| F | H | Cl | $CH_2C{\equiv}CH$ | S | |
| F | H | F | $CH_2C{\equiv}CH$ | O | |
| Cl | H | F | H | S | |
| Cl | H | F | $CH_3$ | S | |
| Cl | H | F | $CH_2CH_3$ | S | |
| Cl | H | F | $CH(CH_3)_2$ | S | |
| Cl | H | F | $CH_2CH_2CH_3$ | S | |
| Cl | H | F | $CH_2C{\equiv}CH$ | S | |
| Cl | H | F | $CH(CH_3)C{\equiv}CH$ | S | |
| Cl | H | F | $CH_2C{\equiv}CH$ | S | |
| Cl | H | F | $CF_2CHF_2$ | S | |
| Cl | H | F | $CH_2CH{=}CHCH_3$ | S | |
| Cl | H | Cl | $CH_2C{\equiv}CH$ | S | |
| $OCH_3$ | H | F | $CH_2C{\equiv}CH$ | S | |
| $OCH_3$ | H | F | $CH_3$ | S | |
| Br | H | F | $CH_2C{\equiv}CH$ | S | |
| Br | H | F | $CH_3$ | S | |
| Br | H | F | $CH(CH_3)C{\equiv}CH$ | S | |
| Br | H | F | $CH_2CH_3$ | S | |
| Br | H | F | $CH_2CH_2CH_3$ | S | |
| Br | H | Cl | $CH_2C{\equiv}CH$ | S | |
| Br | H | F | $CH_2C{\equiv}CH$ | O | |

TABLE 6

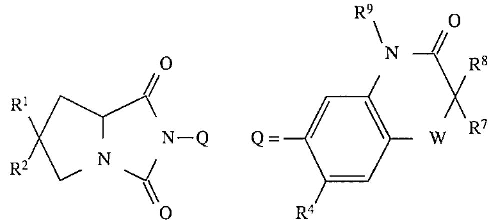

| $R^1$ | $R^2$ | $R^4$ | $R^7$ | $R^8$ | $R^9$ | w | melting point °C. |
|---|---|---|---|---|---|---|---|
| F | H | F | H | H | $CH_3$ | O | |
| F | H | F | H | H | $CH_2CH_3$ | O | |
| F | H | F | H | H | $CH_2CH_2CH_3$ | O | |
| F | H | F | H | H | $CH(CH_3)_2$ | O | |
| F | H | F | H | H | $CH_2C{\equiv}CH$ | O | 189–191 (2R, 7S-Konfiguration) |
| F | H | F | H | H | $CH_2C{=}CH_2$ | O | |
| F | H | F | H | H | $CH(CH_3)C{\equiv}CH$ | O | |
| F | H | F | $CH_3$ | H | $CH_2C{\equiv}CH$ | O | |
| F | H | Cl | H | H | $CH_2C{\equiv}CH$ | O | |
| F | H | F | H | H | $CH_2C{\equiv}CH$ | S | |
| OH | H | F | H | H | $CH_2C{\equiv}CH$ | O | 207–209 |
| F | H | F | $CH_3$ | $CH_3$ | $CH_2C{\equiv}CH$ | O | |
| Cl | H | F | H | H | H | O | |
| Cl | H | F | H | H | $CH_3$ | O | |
| Cl | H | F | H | H | $CH_2CH_3$ | O | |
| Cl | H | F | H | H | $CH_2C{\equiv}CH$ | O | |
| Cl | H | F | H | H | $CH(CH_3)_2$ | O | |
| Cl | H | F | H | H | $CH(CH_3)C{\equiv}CH$ | O | |
| Cl | H | F | H | H | $CH_2CH{=}CH_2$ | O | |
| Cl | H | F | $CH_3$ | H | $CH_2CH{\equiv}CH$ | O | |
| Cl | H | F | $CH_3$ | $CH_3$ | $CH_2C{\equiv}CH$ | O | |
| Cl | H | Cl | H | H | $CH_2C{\equiv}CH$ | O | |
| Cl | H | F | H | H | $CH_2C{\equiv}CH$ | S | |
| $OCH_3$ | H | F | H | H | $CH_2C{\equiv}CH$ | O | |
| Br | H | F | H | H | $CH_3$ | O | |
| Br | H | F | H | H | $CH_2CH_2CH_3$ | O | |
| Br | H | F | $CH_3$ | H | $CH_2C{\equiv}CH$ | O | |
| Br | H | F | $CH_3$ | $CH_3$ | $CH_2C{\equiv}CH$ | O | |
| Br | H | Cl | H | H | $CH_2C{\equiv}CH$ | O | |
| Br | H | Cl | H | H | $CH_2C{\equiv}CH$ | S | |
| $OSi(CH_3)_3$ | H | F | H | H | $CH_2C{\equiv}CH$ | O | |
| $OSi(CH_3)_3$ | H | F | H | H | $CH_2C{\equiv}CH$ | S | |
| F | F | F | H | H | $CH_2C{\equiv}CH$ | O | glass (2R-Konfiguration) |
| F | F | F | H | H | $CH_2CH{=}CH_2$ | O | |
| F | F | F | H | H | $CH_2CO_2CH_3$ | O | |

TABLE 7

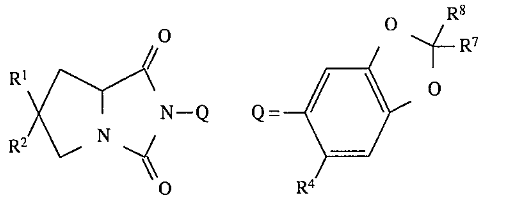

| $R^1$ | $R^2$ | $R^4$ | $R^7$ | $R^8$ | melting point °C. |
|---|---|---|---|---|---|
| F | H | H | F | F | |
| F | H | F | F | F | |
| F | H | F | H | H | |
| Cl | H | H | F | F | |
| Cl | H | F | F | F | |
| Cl | H | F | H | H | |
| $OCH_3$ | H | H | F | F | |
| $OCH_3$ | H | F | F | F | |
| $OCH_3$ | H | F | H | H | |
| Br | H | H | F | F | |
| Br | H | F | F | F | |
| Br | H | F | H | H | |
| F | F | F | H | H | |
| F | F | F | F | F | |
| F | F | H | F | F | |

TABLE 8

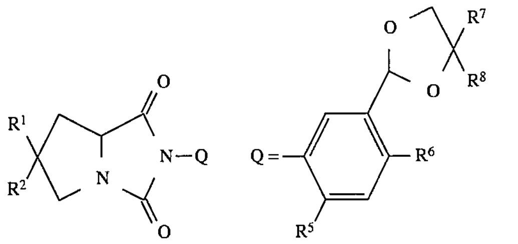

| $R^1$ | $R^2$ | $R^5$ | $R^6$ | $R^7$ | $R^8$ | melting point °C. |
|---|---|---|---|---|---|---|
| F | H | H | H | $CO_2CH_3$ | $CH_3$ | |
| Cl | H | H | H | $CO_2CH_3$ | $CH_3$ | |
| F | H | H | H | $CO_2C_2H_5$ | $CH_3$ | |
| F | H | H | H | $CO_2C_2H_5$ | H | |
| F | H | H | H | $CO_2(CH_2)_2CH_3$ | $CH_3$ | |
| Cl | H | H | H | $CO_2(CH_2)_2CH_3$ | H | |
| Cl | H | H | H | $CO_2(CH_2)_3CH_3$ | $CH_3$ | |
| F | H | H | H | $CO_2(CH_2)_3CH_3$ | H | |
| F | H | H | H | $CO_2CH_2C{\equiv}CH$ | $CH_3$ | |
| F | H | H | Cl | $CO_2CH_3$ | $CH_3$ | |
| F | H | H | Cl | $CO_2C_2H_5$ | $CH_3$ | |
| F | H | H | Cl | $CO_2(CH_2)_2CH_3$ | $CH_3$ | |
| Cl | H | H | Cl | $CO_2(CH_2)_3CH_3$ | $CH_3$ | |
| F | H | H | Cl | $CO_2CH_2C{\equiv}CH$ | $CH_3$ | |
| F | H | F | Cl | $CO_2CH_3$ | $CH_3$ | |
| F | H | F | Cl | $CO_2C_2H_5$ | $CH_3$ | |
| F | F | F | Cl | $CO_2CH_3$ | $CH_3$ | |
| F | F | F | Cl | $CO_2CH_2CH_3$ | $CH_3$ | |
| F | F | F | Cl | $CO_2CH_2CH_2CH_3$ | $CH_3$ | |
| F | F | F | Cl | $CO_2(CH_2)_3CH_3$ | $CH_3$ | |
| F | F | Cl | Cl | $CO_2(CH_2)_3CH_3$ | $CH_3$ | |
| F | H | F | Cl | $CO_2(CH_2)_2CH_3$ | $CH_3$ | |
| F | H | F | Cl | $CO_2(CH_2)_2CH_3$ | H | |
| F | H | F | Cl | $CO_2CH_2C{\equiv}CH$ | $CH_3$ | |
| F | H | F | Cl | $CO_2CH(CH_3)C{\equiv}CH$ | $CH_3$ | |
| F | H | F | Cl | $CO_2CHCH{=}CH_2$ | $CH_3$ | |
| F | H | F | Cl | $CO_2CH(CH_3)_2$ | $CH_3$ | |
| F | H | F | Cl | $CO_2(CH_2)_3CH_3$ | $CH_3$ | |

TABLE 8-continued

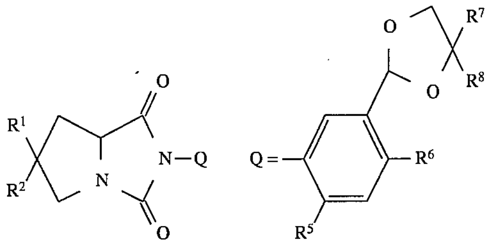

| $R^1$ | $R^2$ | $R^5$ | $R^6$ | $R^7$ | $R^8$ | melting point °C. |
|---|---|---|---|---|---|---|
| F | H | F | Cl | $CO_2CH(CH_3)CH_2CH_3$ | $CH_3$ | |
| Cl | H | F | Cl | $CO_2(CH_2)_2CH_3$ | $CH_3$ | |
| Cl | H | F | Cl | $CO_2(CH_2)_3CH_3$ | $CH_3$ | |
| Cl | H | F | Cl | $CO_2CH(CH_3)_2$ | $CH_3$ | |
| Br | H | F | Cl | $CO_2(CH_2)_2CH_3$ | $CH_3$ | |
| Cl | H | F | Cl | $CO_2CH_3$ | $CH_3$ | |
| Cl | H | F | Cl | $CO_2CH_2CH_3$ | $CH_3$ | |
| Br | H | F | Cl | $CO_2(CH_2)_3CH_3$ | $CH_3$ | |
| Br | H | F | Cl | $CO_2(CH_2)_2CH_3$ | H | |
| Br | H | F | Cl | $CO_2CH_3$ | $CH_3$ | |
| $OCH_3$ | H | F | Cl | $CO_2CH_3$ | $CH_3$ | |
| Br | H | F | Cl | $CO_2CH_2CH_3$ | $CH_3$ | |
| $OCH_3$ | H | F | Cl | $CO_2(CH_2)_3CH_3$ | $CH_3$ | |
| Cl | H | F | Cl | $CO_2CH_2C{\equiv}CH$ | $CH_3$ | |
| Br | H | F | Cl | $CO_2CH_2C{\equiv}CH$ | $CH_3$ | |
| Cl | H | F | Cl | $CO_2CH(CH_3)C{\equiv}CH$ | $CH_3$ | |
| Cl | H | F | Cl | $CO_2CH_2CH{=}CH_2$ | $CH_3$ | |
| Cl | H | H | H | $CO_2CH_2C{\equiv}CH$ | $CH_3$ | |
| Cl | H | H | Cl | $CO_2CH_2C{\equiv}CH$ | $CH_3$ | |
| Br | H | H | Cl | $CO_2CH_2C{\equiv}CH$ | $CH_3$ | |
| Br | H | F | Cl | $CO_2CH(CH_3)C{\equiv}CH$ | $CH_3$ | |
| $OCH_3$ | H | F | Cl | $CO_2CH_2C{\equiv}CH$ | $CH_3$ | |

TABLE 9

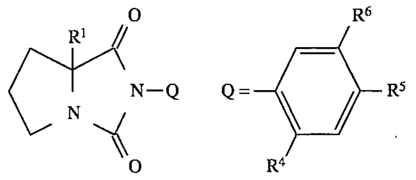

| $R^1$ | $R^4$ | $R^5$ | $R^6$ | melting point °C. |
|---|---|---|---|---|
| $CH_3$ | F | Cl | $CO_2CH(CH_3)_2$ | 95–99 [2R-Konfiguration, $[\alpha]_D^{20} = -14{,}3$ (c = 0,5 in $CH_3OH$)] |
| $CH_3$ | F | Cl | $CO_2CH(CH_3)_2$ | 97–99 [2S-Konfiguration, $[\alpha]_D^{20} = +13{,}8$ (c = 0,5 in $CH_3OH$)] |
| $CH_3$ | F | Cl | $OCH_2C{\equiv}CH$ | |
| $CH_3$ | F | Cl | $OCH(CH_3)C{\equiv}CH$ | |
| $CH_3$ | F | Cl | $SCH_2CO_2CH_3$ | |
| $CH_3$ | F | Cl | $OCH_2CH{=}CH_2$ | |

Formulations

Compounds of this invention will generally be used in formulation with an agriculturally suitable carrier comprising a liquid or solid diluent or an organic solvent. Use formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., “Handbook of Insecticide Dust Diluents and Carriers”, 2nd Ed., Dorland Books:, Caldwell, N.J. Typical liquid diluents and solvents are described in Marsden, “Solvents Guide”, 2nd Ed., Interscience, New York, 1950. “McCutcheon's Detergents and Emulsifiers Annual”, Allured Publ. Corp., Ridgewood, N.J, as well as Sisely and Wood, “Encyclopedia of Surface Active Agents”, Chemical Publ. Co., Inc,, New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and usually grinding as in a hammer mill or fluid energy mill. Water-dispersible granules can be produced be agglomerating a fine powder composition; see for example. Cross et al., “Pesticide Formulations”, Washington, D.C., 1988, pp 251–259. Suspensions are prepared by wet-milling; see, for example, U.S. 3.060,084. Granules and pellets can be made by spraying the active material upon preformed granular carriers or by agglomeration techniques. See Browning, “Agglomeration”, *Chemical Engineering,* Dec. 4, 1967, pp 147–148, “Perry's Chemical Engineer's Handbook”, 4th Ed., HcGraw-Hill, New York, 1963, pages 8–57 and following, and WO 91/13546. Pellets can be prepared as described in U.S. Pat. No. 4,172,714. Water-dispersible and water-soluble granules can also be prepared as taught in DE 32 46 493.

For further information regarding the art of formulation, see U.S. Pat. No. 3,235,361, Col. 6, line 16 through Col. 7, line 19 and Examples 10–41: U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, “Weed Control as a Science”, John Wiley and Sons, Inc., New York. 1961, pp 81–96; and Hance et al., “Weed Control Handbook”, 8th Ed., Blackwell Scientific Publications, Oxford, 1989.

In the following Examples, all percentages are by weight and all formulations are worked up in conventional ways.

EXAMPLE A

Wettable Powder

| | |
|---|---|
| 4-(4'-chloro-2'-fluoro-5'-carboisopropoxyphenyl)-7-chloro-3,5-dioxo-1,4-diazabicyclo-[3.3.0]octane | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended and packaged.

EXAMPLE B

Wettable Powder

| | |
|---|---|
| 4-(4'-chloro-2'-fluoro-5'-carboisopropoxyphenyl)-7-chloro-3,5-dioxo-1,4-diazabicyclo-[3.3.0]octane | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce Particles essentially all below 10 microns in diameter. The product is reblended before packaging.

EXAMPLE C

Granule

| | |
|---|---|
| Wettable Powder of Example 8 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE D

Extruded Pellet

| | |
|---|---|
| 4-(4'-chloro-2'-fluoro-5'-carboisopropoxyphenyl)-7-chloro-3,5-dioxo-1,4-diazabicyclo-[3.3.0]octane | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE

Low Strength Granule

| | |
|---|---|
| 4-(4'-chloro-2'-fluoro-5'-carboisopropoxyphenyl)-7-chloro-3,5-dioxo-1,4-diazabicyclo-[3.3.0]octane | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE F

Granule

| | |
|---|---|
| 4-(4'-chloro-2'-fluoro-5'-carboisopropoxyphenyl)-7-chloro-3,5-dioxo-1,4-diazabicyclo-[3.3.0]octane | 80% |
| wetting agent | 1% |
| crude lingninsulfonate salt (containing 5–20% of the natural sugars) | 10% |
| attapulgite clay | 9% |

The ingredients are blended and milled to pass through a 0.15 mm (100 mesh) screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionall with heat, until the water content is reduced to the desired level, generally less than 1%. The material is then discharged, screened to the desired size range, generally 1.4 mm–0.15 mm (14–100 mesh), and packaged for use.

EXAMPLE G

Aqueous Suspension

| | |
|---|---|
| 4-(4'-chloro-2'-fluoro-5'-carboisopropoxyphenyl)-7-chloro-3,5-dioxo-1,4-diazabicyclo-[3.3.0]octane | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and :ground together in a sand mill to produce particles essentially all under 5 microns in size.

EXAMPLE H

High Strength Concentrate

| | |
|---|---|
| 4-(4'-chloro-2'-fluoro-5'-carboisopropoxyphenyl)-7-chloro-3,5-dioxo-1,4-diazabicyclo-[3.3.0]octane | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE I

Wettable Powder

| | |
|---|---|
| 4-(4'-chloro-2'-fluoro-5'-carboisopropoxyphenyl)-7-chloro-3,5-dioxo-1,4-diazabicyclo-[3.3.0]octane | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen (0.3 mm) and then packaged.

EXAMPLE J

Wettable Powder

| | |
|---|---|
| 4-(4'-chloro-2'-fluoro-5'-carboisopropoxyphenyl)-7-chloro-3,5-dioxo-1,4-diazabicyclo-[3.3.0]octane | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE K

Oil Suspension

| | |
|---|---|
| 4-(4'-chloro-2'-fluoro-5'-carboisopropoxyphenyl)-7-chloro-3,5-dioxo-1,4-diazabicyclo-[3.3.0]octane | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE L

Dust

| | |
|---|---|
| 4-(4'-chloro-2'-fluoro-5'-carboisopropoxyphenyl)-7-chloro-3,5-dioxo-1,4-diazabicyclo-[3.3.0]octane | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE M

Oil Suspension

| | |
|---|---|
| 4-(4'-chloro-2'-fluoro-5'-carboisopropoxyphenyl)-7-chloro-3,5-dioxo-1,4-diazabicyclo-[3.3.0]octane | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Utility

The compounds of the present invention are active herbicides. They have utility for broadspectrum preemergence and/or postemergence weed control in areas where complete control of all vegetation is desired, such as around industrial complexes, storage areas, parking lots, drive-in theaters, around billboards, fence rows, highway and railroad structures. Some of the compounds have utility for selective weed control in crops such as rice, wheat, barley, corn, soybeans, sugarbeets, cotton, peanut, all plantation crops including coffee, cocoa, sugarcane, oil palm, rubber, citrus, grapes, fruit trees, nut trees, banana, plantain, pineapple and conifers such as loblolly pine.

The compounds can be applied as a preemergence and/or postemergence treatment using techniques of banding, directed sprays or broadcast applications. The rates of application for the compounds of the invention are determined by a number of factors, including their use as selective or general herbicides, the crop species involved, the types-of weeds to be controlled, weather, climate, formulations selected, mode of application, amount of foliage present, etc. By selecting the appropriate rate which would be apparent to one skilled in the art, the compounds of this invention can be used in areas where complete control of all vegetation is desired, such as around fuel storage tanks, ammunition depots, industrial storage areas, oil well sites, drive-in theaters, around billboards, highway and railroad structures and in fence rows. Alternatively, by selecting the proper rates and adjuvants, the compounds of this invention can be used for selective weeds control in peanuts and plantation corps such as citrus, sugarcane, coffee, oil palm, rubber, cocoa, grapes, fruit trees, nut trees, pineapple and banana. In general, the subject compounds are applied at levels of around 0.001 to 20 kg/ha, with a preferred rate range of 0.01 to 2 kg/ha rate. One skilled in the art can select the proper rates for a given situation.

The compounds of this invention may be used in combination with other herbicides listed below. They are particularly useful in combination with triazine, triazole, uracil, urea, amide, carbamate, bipyridylium, phenoxy, sulfonylurea and imidazole types for total vegetation control in plantation and other crops. The compounds may also be used in combination with mefluidide, glyphosate or gluphosinate.

A mixture of one or more of the following herbicides with a compound of this invention may be particularly useful for weed control. Examples of other herbicides with which compounds of this invention can be formulated are: acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bomoxynil heptanoate, bromoxynil octanoate, butachlor, buthidazole, buttalin, butylate, cacodylic acid, 2-chloro-N,N-di-2-propenylacetamide, 2-chloroallyl dlethyldithiocarbamate, chloramben, chlorbromuron. chloridazon, chlorimuron ethyl, chlormethoxynil, chlornitrofen, chloroxuron, chlorpropham, chlorsulfuron, chlortoluron, cinmethylin, cinosulfuron, clethodium, clomazone, cloproxydim, clopyralid, calcium salt or methylarsonic acid, cyanazine, cycloate, cyluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorbrop, diclofop, diethatyl, difenzoquat, diflufenican, dimepiperate, dinitramine, dinoseb, diphenamid, diprobetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazipop, fluazipop-P, fluchloralin, flumesulam, flumipropyn, fluometuron, fluorochloridone, fuorodifen, fluoroglycofen, flupoxam, fluridone, fluoroxypyr, fluzasulfuron, fomesafen, fosamine, glyphosate, haloxylop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)-3,5-pyridinedicarbothioate, mecoprop, mefenacet, mefluidide, methalbropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, nabropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluormethyl)phenoxy]-2-nitroacetophenone oxime-0-acetic acid methyl ester, pretilachlor, brimisulfuron, brocyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron secbumeton, sethoxydim, siduron, simazine, 1-(a,a-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydlm, triasulfuron, tribehuron methyl, triclopyr, tridiphane, trifluralin, trimeturon, (2,4-dichlorophenoxy)acetic acid, 4-(2,4-dichlorophenoxy)butanoic acid, vernolate, and xylachlor.

The herbicidal properties of the subject compounds were discovered in a number of greenhouse tests. The test procedures and results are as follows:

Biological Tables
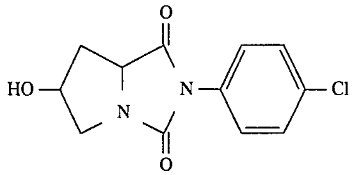
compound 1
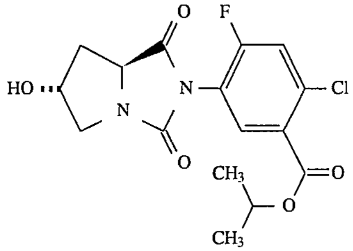
compound 2
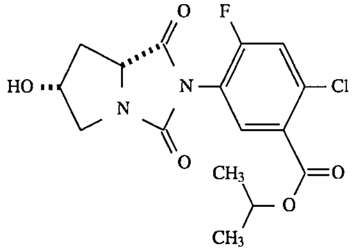
compound 3
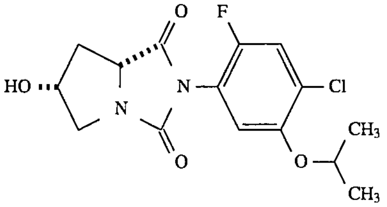
compound 4
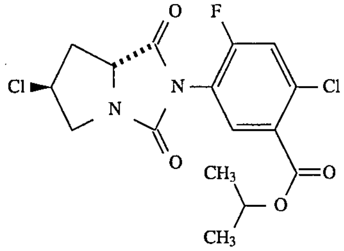
compound 5
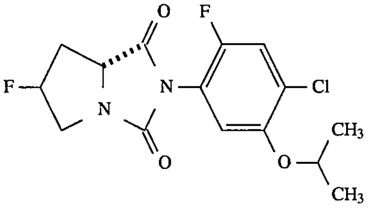
compound 6
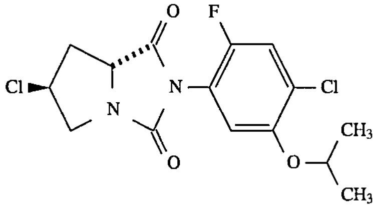
compound 7
-continued
Biological Tables
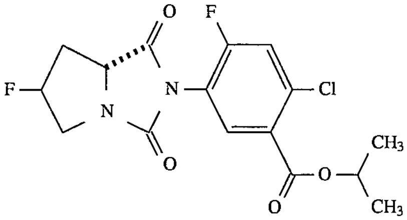
compound 8
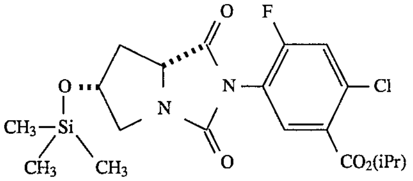
compound 9
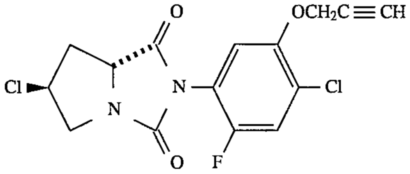
compound 10
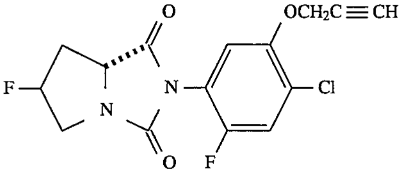
compound 11
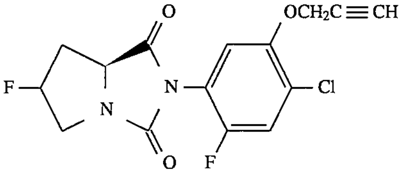
compound 12
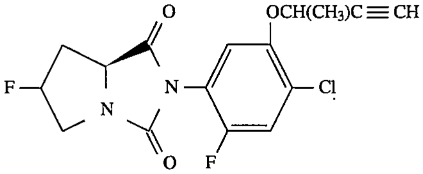
compound 13
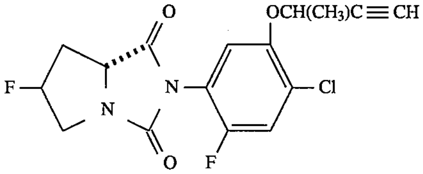
compound 14
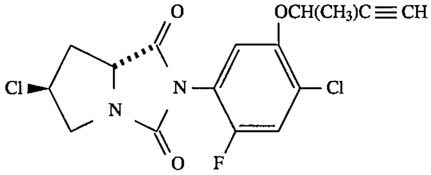
compound 15

-continued

Biological Tables

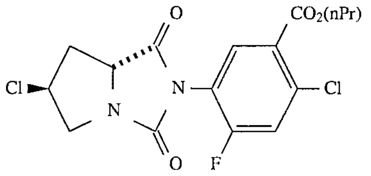

compound 16

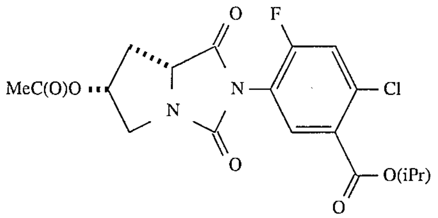

compound 17

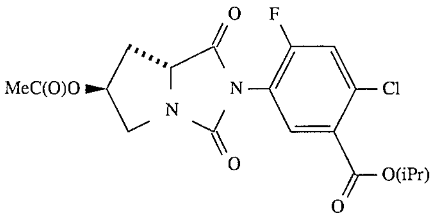

compound 18

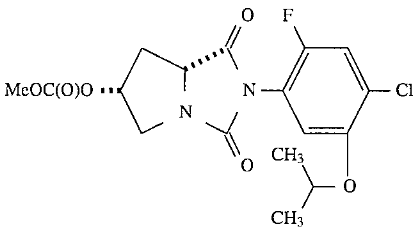

compound 19

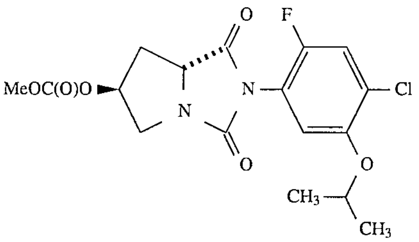

compound 20

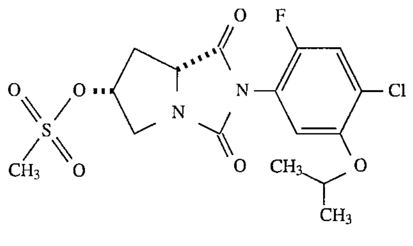

compound 21

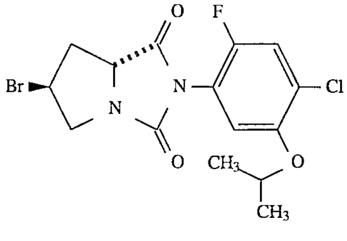

compound 22

-continued

Biological Tables

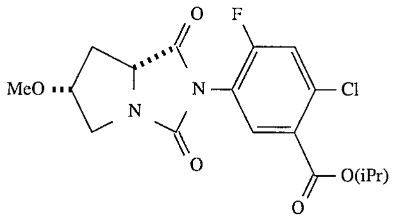

compound 23

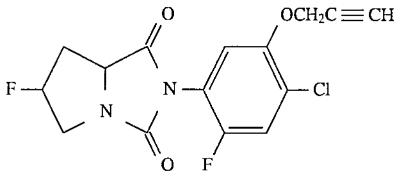

compound 24

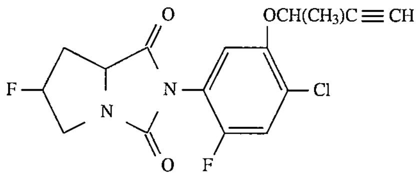

compound 25

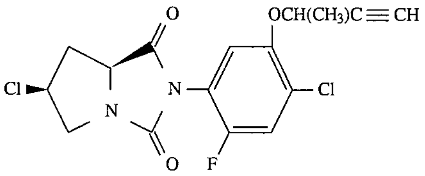

compound 26

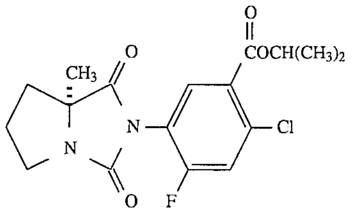

compound 27

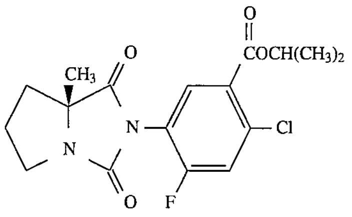

compound 28

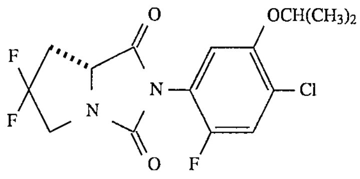

compound 29

Test procedure

Seeds of crabgrass (Digitaria spp.), barnyardgrass (*Echinochloa crus-galli*), giant foxtail (*Setaria faberii*), wild oats (*Arena fatua*), cheatgrass (*Bromus secalinus*), velvetleaf (*Abutilon theophrasti*), morningglory (Ipomoea spp.), cocklebur (*Xanthium pensylvanicum*) and sorghum. Nutsedge tubers were planted and treated preemergence with the test chemicals dissolved in a non-phytotoxic solvent. At the same time, these weed species were treated with a soil/foliage application. At the time of treatment, the plants ranged in height from 2to 18 cm. Treated plants and controls were maintained in a greenhouse for sixteen days, after which all species were visually rated for response to treatment and compared to controls. The ratings, summarized in Table A–$E_4$, are based on a numerical scale extending from 0=no injury, to 10=complete kill.

The accompanying descriptive symbols have the following meanings:

C=chlorosis/necrosis;

B=burn

H=formative effect;

G=growth retardation:

E=emergence inhibition.

TABLE A postemergence (application rate 2 kg a.i./ha)

| | Comp. 1 | Comp. 2 | Comp. 3 | Comp. 4 | Comp. 5 | Comp. 6 | Comp. 7 | Comp. 8 | Comp. 9 | Comp. 10 | Comp. 11 | Comp. 12 |
|---|---|---|---|---|---|---|---|---|---|---|---|---|
| Barnyardgrass | 1B | 6B | 8B | 6B | 10C | 10C | 10B | 10C | 8B | 10 | 10 | 10 |
| Cheat grass | 1B | 1B | 1B | 2B | 10C | 10C | 10B | 10C | 7B | 10 | 10 | 10 |
| Cocklebur | — | 4B | — | — | 10C | 10C | — | 10C | — | 10 | 10 | 10 |
| Morningglory | 0 | 7B | 6B | 8B | 10C | 10C | 10B | 10C | 9B | 10 | 10 | 10 |
| Sorghum | 1B | 2B | 2B | 2B | 10C | 10C | 9B | 10C | 4B | 10 | 10 | 10 |
| Giant foxtail | 1B | 4B | 7B | 8B | 10C | 10C | 10B | 10C | 9B | 10 | 10 | 10 |
| Crabgrass | 1B | 6B | 7B | 3B | 10C | 10C | 10B | 10C | 8B | 10 | 10 | 10 |
| Velvetleaf | 0 | 5B | 8B | 7B | 10C | 10C | 10B | 10C | 8B | 10 | 10 | 10 |
| Wild oats | 1B | 2B | 2B | 2B | 10C | 10C | 10B | 10C | 6B | 10 | 10 | 10 |

| | Comp. 13 | Comp. 14 | Comp. 15 | Comp. 16 |
|---|---|---|---|---|
| Barnyardgrass | 10 | 10 | 10 | 10 |
| Cheat grass | 10 | 10 | 10 | 10 |
| Cocklebur | 10 | 10 | 10 | 10 |
| Morningglory | 10 | 10 | 10 | 10 |
| Sorghum | 10 | 10 | 10 | 10 |
| Giant foxtail | 10 | 10 | 10 | 10 |
| Crabgrass | 10 | 10 | 10 | 10 |
| Velvetleaf | 10 | 10 | 10 | 10 |
| Wild oats | 10 | 10 | 10 | 10 |

TABLE B preemergence (application rate 2 kg a.i./ha)

| | Comp. 1 | Comp. 2 | Comp. 3 | Comp. 4 | Comp. 5 | Comp. 6 | Comp. 7 | Comp. 8 | Comp. 9 | Comp. 10 | Comp. 11 | Comp. 12 |
|---|---|---|---|---|---|---|---|---|---|---|---|---|
| Barnyardgrass | 0 | 8H, 2C | 9H, 3C | 9H, 3C | 10C | 10C | 10C | 10C | 9C, 5H | 10 | 10 | 10 |
| Cheat grass | 0 | 0 | 5H, 1C | 6G | 10C | 10C | 10C | 10C | 3H | 10 | 10 | 10 |
| Cocklebur | — | 6H, 2C | — | — | 10C | 10C | 10C | 10C | 0 | 10 | 10 | 10 |
| Morningglory | 0 | 3G, 1C | 2G, 1H | 0 | 10C | 10C | 10C | 10C | 1C | 10 | 10 | 10 |
| Sorghum | 0 | 3H, 1C | 5H, 1C | 3G | 10C | 10C | 10C | 10C | 0 | 10 | 10 | 10 |
| Giant foxtail | 0 | 3H | 10C | 9H, 3C | 10E | 10E | 10C | 10C | 10C | 10 | 10 | 10 |
| Crabgrass | 0 | 9H | 10C | 8H, 1C | 10C | 10C | 10C | 10C | 9C | 10 | 10 | 10 |
| Velvetleaf | 0 | 10C | 10C | 9C | 10E | 10E | 10E | 10E | 9C | 10 | 10 | 10 |
| Wild oats | 0 | 0 | 4H, 1C | 4G, 2C | 10C | 10C | 10C | 10C | 0 | 10 | 10 | 10 |

| | Comp. 13 | Comp. 14 | Comp. 15 | Comp. 16 |
|---|---|---|---|---|
| Barnyardgrass | 10 | 10 | 10 | 10 |
| Cheat grass | 10 | 10 | 10 | 10 |
| Cocklebur | 10 | 10 | 10 | 10 |
| Morningglory | 10 | 10 | 10 | 10 |
| Sorghum | 10 | 10 | 10 | 10 |
| Giant foxtail | 10 | 10 | 10 | 10 |
| Crabgrass | 10 | 10 | 10 | 10 |
| Velvetleaf | 10 | 10 | 10 | 10 |
| Wild oats | 10 | 10 | 10 | 10 |

TABLE C

| | postemergence (application rate 0.2 kg a.i./ha) | | | | | | |
|---|---|---|---|---|---|---|---|
| | Comp. 17 | Comp. 18 | Comp. 19 | Comp. 20 | Comp. 21 | Comp. 22 | Comp. 23 |
| Corn | 2B | 2B | 1B | 0 | 1B | 6B | 2B |
| Wheat | 3B | 1B | 0 | 0 | 2B | 6B | 2B |
| Barnyardgrass | 5B | 2B | 1B | 2B | 1B | 9B | 4B |
| Cheat grass | 3B | 2B | 0 | 0 | 1B | 5B | 3B |
| Cocklebur | 2B | 5B | 0 | 0 | 1B | 9B | 3B |
| Morningglory | 5B | 6B | 2B | 1B | 1B | 10B | 6B |
| Sorghum | — | — | 0 | 0 | 1B | — | 3B |
| Giant foxtail | 4B | 3B | 1B | 1B | 1B | 7B | 4B |
| Crabgrass | 5B | 2B | 1B | 1B | 2Bb | 8B | 4B |
| Velvetleaf | 3B | 4B | 1B | 1B | 1B | 10B | 4B |
| Wild oats | 2B | 1B | 0 | 0 | 1B | 5B | 1B |

TABLE D

| | preemergence (application rate 0.2 kg a.i./ha) | | | | | | |
|---|---|---|---|---|---|---|---|
| | Comp. 17 | Comp. 18 | Comp. 19 | Comp. 20 | Comp. 21 | Comp. 22 | Comp. 23 |
| Corn | 0 | 0 | 0 | 0 | 0 | 2C | 1G |
| Wheat | 0 | 0 | 0 | 0 | 0 | 3C | 0 |
| Barnyardgrass | 0 | 0 | 0 | 0 | 0 | 9H, 5C | 1H |
| Cheat grass | 0 | 0 | 0 | 0 | 0 | 5C | 0 |
| Cocklebur | 0 | 0 | 0 | 0 | 0 | 7G | 0 |
| Morningglory | 0 | 0 | 0 | 0 | 0 | 3H, 2C | 3G |
| Sorghum | 0 | 0 | 0 | 0 | 0 | 5G, 2C | 0 |
| Giant foxtail | 1H | 0 | 0 | 2G | 0 | 10H | 1H |
| Crabgrass | 4G | 0 | 0 | 2G | 0 | 10H | 0 |
| Velvetleaf | 0 | 0 | 0 | 0 | 0 | 9C | 0 |
| Wild oats | 0 | 0 | 0 | 0 | 0 | 6C | 0 |

TABLE $E_1$

| | postemergence (rate 200 g/ha) | | | |
|---|---|---|---|---|
| | Comp. 26 | Comp. 27 | Comp. 28 | Comp. 29 |
| Barley | 2B | 2B | 3B | 9B |
| Barnyardgrass | 4B | 1B | 2B | 10B |
| Bedstraw | 10B | 3B | 5B | 10B |
| Blackgrass | 2B | 1B | 3B | 9B |
| Cheatgrass | 2B | 1B | 3B | — |
| Chickweed | 6B | 3B | — | 9B |
| Cocklebur | 9B | 1B | 4B | 10B |
| Corn | 2B | 2B | 3B | 8B |
| Cotton | 100B | 9B | 9B | 10B |
| Crabgrass | 3B | 2B | 2B | 10B |
| Downy brome | — | — | — | 9B |
| Giant foxtail | 3B | 3B | 3B | 9B |
| Lambsquarter | 8B | 2B | 7B | 10B |
| Morningglory | 10B | 2B | 5B | 10B |
| Nutsedge | 3B | 0 | 1B | 6B |
| Rape | 10B | 2B | 2B | 10B |
| Rice | 5B | 3B | 3B | 10B |
| Sorghum | 3B | 3B | 4B | 10B |
| Soybean | 6B | 2B | 7B | 10B |
| Sugar beet | 10B | 2B | 6B | 10B |
| Velvetleaf | 3B | 5G | 3B | 10B |
| Wheat | 4B | 0 | 3B | 9B |
| Wild buckwheat | 10B | 1B | 6B | 10B |
| Wild oat | 2B | 2B | 2B | 10B |

TABLE $E_2$

| | preemergence (rate 200 g/ha) | | | |
|---|---|---|---|---|
| | Comp. 26 | Comp. 27 | Comp. 28 | Comp. 29 |
| Barley | 0 | 0 | 0 | 5C |
| Barnyardgrass | 1H | 3G | 0 | 10C |
| Bedstraw | 9 | 2G | 10C | 10C |
| Blackgrass | 0 | 0 | 1C | 9C |
| Cheatgrass | 8G | 0 | 1C | — |
| Chickweed | 10C | 0 | 0 | 10E |
| Cocklebur | 0 | 0 | 0 | 7G |
| Corn | 0 | 2G | 2G | 8H |
| Cotton | 0 | 0 | 0 | 10C |
| Crabgrass | 2H | 1H | 5G | 10C |
| Downy brome | — | — | — | 10C |
| Giant foxtail | 0 | 3G | 4G | 10C |
| Lambsquarter | 10C | 5G | 10C | 10E |
| Morningglory | 0 | 0 | 0 | 10C |
| Nutsedge | 0 | 0 | 0 | 4C |
| Rape | 0 | 1H | 2G | 10E |
| Rice | 2G | 0 | 0 | 7G |
| Sorghum | 0 | 0 | 0 | 9C |
| Soybean | 0 | 0 | 0 | 9H |
| Sugar beet | 0 | 1H | 9C | 10C |
| Velvetleaf | 10C | 0 | 0 | 10C |
| Wheat | 2C | 0 | 0 | 7C |
| Wild buckwheat | 10C | 0 | 10C | 10E |
| Wild oat | 2G | 0 | 0 | 9C |

TABLE $E_3$

| | postemergence (rate 50 g/ha) | | | |
|---|---|---|---|---|
| | Comp. 26 | Comp. 27 | Comp. 28 | Comp. 29 |
| Barley | 2B | 0 | 1B | 9B |
| Barnyardgrass | 3B | 1B | 1B | 9B |
| Bedstraw | 8B | 1B | 1B | 10B |
| Blackgrass | 1B | 0 | 1B | 7B |
| Cheatgrass | 1B | 1B | 1B | — |
| Chickweed | 3B | 1B | 1B | 9B |
| Cocklebur | 7B | 1B | 1B | 10B |
| Corn | 2B | 1B | 1B | 8B |
| Cotton | 10 | 1B | 8B | 10B |
| Crabgrass | 2B | 1B | 1B | 8B |
| Downy brome | — | — | — | 6B |
| Giant foxtail | 2B | 1B | 1B | 8B |
| Lambsquarter | 7B | 1B | 4B | 10B |
| Morningglory | 9B | 1B | 1B | 10B |
| Nutsedge | 1B | 0 | 0 | 3B |
| Rape | 10B | 0 | 2B | 10B |
| Rice | 2B | 1B | 3B | 9B |
| Sorghum | 2B | 1B | 2B | 9H |
| Soybean | 8B | 1B | 3B | 10B |
| Sugar beet | 9B | 0 | 1B | 10B |
| Velvetleaf | 2B | 2B | 1B | 10B |
| Wheat | 3B | 0 | 1B | 8B |
| Wild buckwheat | 10B | 1B | 2B | 10B |
| Wild oat | 2B | 0 | 1B | 7B |

TABLE $E_4$

| | preemergence (rate 50 g/ha) | | | |
|---|---|---|---|---|
| | Comp. 26 | Comp. 27 | Comp. 28 | Comp. 29 |
| Barley | 0 | 0 | 0 | 5G |
| Barnyardgrass | 0 | 0 | 0 | 10C |
| Bedstraw | 3G | 0 | 0 | 10C |
| Blackgrass | 0 | 0 | 0 | 9C |
| Cheatgrass | 0 | 0 | 0 | — |
| Chickweed | 0 | 0 | 0 | 10E |
| Cocklebur | 0 | 0 | 0 | — |
| Corn | 0 | 0 | 0 | 8H |
| Cotton | 0 | 0 | 0 | 8H |
| Crabgrass | 2H | 0 | 0 | 10C |
| Downy brome | — | — | — | 9C |
| Giant foxtail | 0 | 0 | 0 | 10C |
| Lambsquarter | 10C | — | 2G | 10E |
| Morningglory | 0 | 0 | 0 | 9H |
| Nutsedge | 0 | 0 | 0 | 6C |
| Rape | 0 | 0 | 0 | 10E |
| Rice | 0 | 0 | 0 | 7G |
| Sorghum | 0 | 0 | 0 | 8H |
| Soybean | 0 | 0 | 0 | 9H |
| Sugar beet | 0 | — | 0 | 9C |
| Velvetleaf | 2G | 0 | 0 | 10C |
| Wheat | 0 | 0 | 0 | 5G |
| Wild buckwheat | 5G | 0 | — | 9C |
| Wild oat | 0 | 0 | 0 | 9C |

Test B

Plastic tray liners with individual planting compartments were filled with planting medium and seeded separately with dallisgrass (*Pasoalum dilatatum*), bermudagrass (*Cynodon dactylon*), annual bluegrass (*Poa annum*), guineagrass (*Panicum maximum*), broadleaf signalgrass (*Brachiaria platyphylla*), goosegrass (*Eleusine indicia*), large crabgrass (*Digitaria sanguinalis*), smooth crabgrass (*D. ischaemum*), sandbur (*Cenchrus echinatus*), itchgrass (*Rottboellia cochinchinensis*), Texas panicum (*P. texanum*), Johnson grass (*Sorghum halepense*), alfalfa (*Medicago sativa*), peanut (*Arachis hypogea*), morningglory (Ipomea sp.), ragweed (*Ambrosia elatior*), putslane (*portulaca oleracea*) and *Pueraris javanica.* Tubers of purple nutsedge (*Cyperus rotundus*) and yellow nutsedge (*C. esculentus*) were also planted separately in individual pots.

The plantings were staggered so that the preemergence and postemergence treatments with the compounds formulated in an non-phytotoxic spray solution were applied on the same day. Plants were visually rated compared with the appropriate controls at the end of the test. The injuring ratings were based on the scale of 0 to 100 where 0 indicates no effect, 20 indicates minimal effect and 100 indicates complete control. The variations in the results for the same compound could be due to the fact that the tests were conducted at different times of the year and on plants at different growth stages. The results are shown in Tables $E_a$–$E_1$.

TABLE $E_a$

| | Compound 4 | |
|---|---|---|
| | 250 Preemergence | 250 g/ha Postemergence |
| Dallisgrass | 0 | 0 |
| Bermudagrass | 0 | 0 |
| Annual bluegrass | 0 | 0 |
| Guineagrass | 0 | 0 |
| Broadleaf signalgrass | 0 | 0 |
| Goosegrass | 0 | 0 |
| Large crabgrass | 0 | 0 |
| Smooth crabgrass | 0 | 0 |
| Sandbur | 0 | 0 |
| Itchgrass | 0 | 0 |
| Johnson grass | 0 | 0 |
| Morningglory | 0 | 0 |
| Ragweed | 0 | 0 |
| Purslane | 0 | 0 |
| Alfalfa | 0 | 0 |
| Peanut | 0 | 0 |
| Purple nutsedge | 0 | 0 |
| Yellow nutsedge | 0 | 0 |

TABLE $E_b$

| | Compound 6 | | | | | |
|---|---|---|---|---|---|---|
| | 500 | 250 | 125 | 500 | 250 | 125 g/ha |
| | Preemergence | | | Postemergence | | |
| Dallisgrass | 100 | 100 | 100 | 100 | 100 | 100 |
| Bermudagrass | 100 | 100 | 100 | 70 | 100 | 70 |
| Annual bluegrass | 100 | 100 | 100 | 50 | 50 | 50 |
| Guineagrass | 100 | 100 | 100 | 80 | 50 | 40 |
| Broadleaf signalgrass | 100 | 100 | 90 | 50 | 60 | 60 |
| Goosegrass | 100 | 100 | 100 | 100 | 90 | 90 |
| Large crabgrass | 100 | 100 | 100 | 100 | 90 | 90 |
| Smooth crabgrass | 100 | 100 | 100 | 90 | 60 | 50 |
| Sandbur | 100 | 100 | 100 | 100 | 90 | 70 |
| Itchgrass | 100 | 100 | 80 | 70 | 50 | 30 |
| Texas panicum | 100 | 100 | 100 | 100 | 80 | 50 |
| Johnson grass | 100 | 100 | 80 | 30 | 30 | 20 |
| Morningglory | 100 | 100 | 90 | 100 | 100 | 100 |
| Purslane | 100 | 100 | 100 | 100 | 100 | 100 |
| Alfalfa | 100 | 100 | 100 | 100 | 100 | 100 |
| Peanut | 0 | 0 | 0 | 70 | 30 | 20 |

TABLE $E_c$

| | Compound 6 | |
|---|---|---|
| | 250 Preemergence | 250 g/ha Postemergence |
| Dallisgrass | 100 | 90 |
| Bermudagrass | 100 | 40 |
| Annual bluegrass | 100 | 20 |
| Guineagrass | 100 | 60 |
| Broadleaf signalgrass | 100 | 30 |
| Goosegrass | 100 | 80 |
| Large crabgrass | 100 | 90 |
| Smooth crabgrass | 100 | 50 |
| Sandbur | 90 | 100 |
| Itchgrass | 100 | 20 |
| Johnson grass | 100 | 20 |
| Morningglory | 100 | 100 |
| Ragweed | 100 | 100 |
| Purslane | 100 | 80 |
| Alfalfa | 100 | 100 |
| Peanut | 0 | 30 |

TABLE $E_d$

| | Compound 6 | |
|---|---|---|
| | 250 Preemergence | 250 g/ha Postemergence |
| Dallisgrass | 100 | 90 |
| Bermudagrass | 100 | 50 |
| Annual bluegrass | 100 | 70 |
| Guineagrass | 100 | 30 |
| Broadleaf signalgrass | 100 | 30 |
| Goosegrass | 100 | 80 |
| Large crabgrass | 100 | 70 |
| Smooth crabgrass | 100 | 50 |
| Sandbur | 100 | 60 |
| Itchgrass | 100 | 30 |
| Johnson grass | 100 | 20 |
| Morningglory | 80 | 100 |
| Ragweed | 100 | 100 |
| Purslane | 100 | 90 |
| Alfalfa | 100 | 100 |
| Peanut | 0 | 70 |
| Purple nutsedge | 40 | 20 |
| Yellow nutsedge | 80 | 80 |

TABLE $E_e$

| | Compound 7 | |
|---|---|---|
| | 250 Preemergence | 250 g/ha Postemergence |
| Dallisgrass | 100 | 20 |
| Bermudagrass | 100 | 0 |
| Annual bluegrass | 80 | 90 |
| Guineagrass | 100 | 0 |
| Broadleaf signalgrass | 100 | 0 |
| Goosegrass | 100 | 0 |
| Large crabgrass | 100 | 0 |
| Smooth crabgrass | 100 | 0 |
| Sandbur | 90 | 0 |
| Itchgrass | 70 | 0 |
| Johnson grass | 60 | 0 |
| Morningglory | 80 | 100 |
| Ragweed | 100 | 100 |
| Purslane | 100 | 100 |
| Alfalfa | 90 | 100 |
| Peanut | 20 | 60 |
| Purple nutsedge | 0 | 20 |
| Yellow nutsedge | 10 | 50 |

TABLE $E_f$

| | Compound 11 | |
|---|---|---|
| | 250 Preemergence | 250 g/ha Postemergence |
| Dallisgrass | 100 | 100 |
| Bermudagrass | 100 | 80 |
| Annual bluegrass | 100 | 60 |
| Guineagrass | 100 | 70 |
| Broadleaf signalgrass | 100 | 80 |
| Goosegrass | 100 | 80 |
| Large crabgrass | 100 | 80 |
| Smooth crabgrass | 100 | 60 |
| Sandbur | 100 | 80 |
| Itchgrass | 100 | 100 |
| Johnson grass | 100 | 100 |
| Morningglory | 100 | 100 |
| Ragweed | 100 | 100 |
| Purslane | 100 | 90 |
| Alfalfa | 100 | 100 |
| Peanut | 60 | 100 |
| Purple nutsedge | 20 | 30 |
| Yellow nutsedge | 80 | 100 |

TABLE $E_g$

| | Compound 12 | |
|---|---|---|
| | 250 Preemergence | 250 g/ha Postemergence |
| Dallisgrass | 90 | 20 |
| Bermudagrass | 20 | 0 |
| Annual bluegrass | 0 | 0 |
| Guineagrass | 80 | 0 |
| Broadleaf signalgrass | 0 | 0 |
| Goosegrass | 100 | 0 |
| Large crabgrass | 90 | 0 |
| Smooth crabgrass | 50 | 0 |
| Sandbur | 60 | 0 |
| Itchgrass | 20 | 0 |
| Johnson grass | 80 | 0 |
| Morningglory | 50 | 20 |
| Ragweed | 30 | 20 |
| Purslane | 100 | 20 |
| Alfalfa | 90 | 0 |
| Peanut | 20 | 0 |
| Purple nutsedge | 0 | 0 |
| Yellow nutsedge | 0 | 0 |

TABLE $E_h$

| | Compound 13 | |
|---|---|---|
| | 250 Preemergence | 250 g/ha Postemergence |
| Dallisgrass | 100 | 0 |
| Bermudagrass | 30 | 0 |
| Annual bluegrass | 30 | 0 |
| Guineagrass | 90 | 0 |
| Broadleaf signalgrass | 20 | 0 |
| Goosegrass | 100 | 0 |
| Large crabgrass | 70 | 0 |
| Smooth crabgrass | 90 | 0 |
| Sandbur | 30 | 0 |
| Itchgrass | 20 | 0 |
| Johnson grass | 80 | 0 |
| Morningglory | 40 | 0 |
| Ragweed | 70 | 0 |
| Purslane | 100 | 30 |
| Alfalfa | 40 | 0 |
| Peanut | 0 | 0 |
| Purple nutsedge | 0 | 0 |
| Yellow nutsedge | 0 | 0 |

TABLE $E_i$

| | Compound 14 | |
|---|---|---|
| | 250 Preemergence | 250 g/ha Postemergence |
| Dallisgrass | 100 | 100 |
| Bermudagrass | 100 | 60 |
| Annual bluegrass | 100 | 70 |
| Guineagrass | 100 | 70 |
| Broadleaf signalgrass | 100 | 60 |
| Goosegrass | 100 | 80 |
| Large crabgrass | 100 | 70 |
| Smooth crabgrass | 100 | 50 |
| Sandbur | 100 | 100 |
| Itchgrass | 100 | 70 |
| Johnson grass | 100 | 50 |
| Morningglory | 100 | 100 |
| Ragweed | 100 | 100 |
| Purslane | 100 | 90 |
| Alfalfa | 100 | 100 |
| Peanut | 50 | 100 |
| Purple nutsedge | 40 | 50 |
| Yellow nutsedge | 80 | 100 |

TABLE $E_j$

| | Compound 22 | |
|---|---|---|
| | 250 Preemergence | 250 g/ha Postemergence |
| Dallisgrass | 90 | 0 |
| Bermudagrass | 90 | 0 |
| Annual bluegrass | 70 | 0 |
| Guineagrass | 100 | 0 |
| Broadleaf signalgrass | 90 | 0 |
| Goosegrass | 100 | 0 |
| Large crabgrass | 100 | 0 |
| Smooth crabgrass | 90 | 0 |
| Sandbur | 90 | 0 |
| Itchgrass | 100 | 0 |
| Johnson grass | 50 | 0 |
| Morningglory | 80 | 60 |
| Ragweed | 100 | 70 |
| Purslane | 100 | 90 |
| Alfalfa | 60 | 90 |
| Peanut | 20 | 30 |
| Purple nutsedge | 0 | 0 |
| Yellow nutsedge | 0 | 0 |

TABLE $E_k$

| | Compound 24 | |
|---|---|---|
| | 250 Preemergence | 250 g/ha Postemergence |
| Dallisgrass | 100 | 90 |
| Bermudagrass | 100 | 50 |
| Annual bluegrass | 100 | 50 |
| Guineagrass | 100 | 70 |
| Broadleaf signalgrass | 100 | 30 |
| Goosegrass | 100 | 80 |
| Large crabgrass | 100 | 60 |
| Smooth crabgrass | 100 | 50 |
| Sandbur | 100 | 80 |
| Itchgrass | 100 | 50 |
| Johnson grass | 100 | 50 |
| Morningglory | 100 | 100 |
| Ragweed | 100 | 100 |
| Purslane | 100 | 90 |
| Alfalfa | 100 | 100 |
| Peanut | 60 | 100 |
| Purple nutsedge | 60 | 20 |
| Yellow nutsedge | 70 | 100 |

TABLE $E_l$

| | Compound 25 | |
|---|---|---|
| | 250 Preemergence | 250 g/ha Postemergence |
| Dallisgrass | 100 | 100 |
| Bermudagrass | 100 | 20 |
| Annual bluegrass | 100 | 0 |
| Guineagrass | 100 | 40 |
| Broadleaf signalgrass | 100 | 40 |
| Goosegrass | 100 | 30 |
| Large crabgrass | 100 | 50 |
| Smooth crabgrass | 100 | 20 |
| Sandbur | 100 | 20 |
| Itchgrass | 100 | 60 |
| Johnson grass | 100 | 20 |
| Morningglory | 100 | 80 |
| Ragweed | 100 | 100 |
| Purslane | 100 | 90 |
| Alfalfa | 100 | 100 |
| Peanut | 60 | 70 |
| Purple nutsedge | 0 | 20 |
| Yellow nutsedge | 60 | 30 |

Test C

Windowsill flats were filled with planting medium and seeded with peanut (*A. hypogea*), gaint foxtail (*Setari faberi*), large crabgrass (*D. Sanguinalis*), guineagrass (*P. maximum*), Johnson grass (*S. haliebense*), nightshade (*solanum nigrum*), morningglory (*Ipomes sp.*) and velvetleaf (*Abutilon theophrasti*). The plantings were treated preemergence with Compound 6 formulated in a non-phytotoxic spray solution. Planets were visually rated 21 and 40 days-after-treatment (DAT) and compared with the appropriate controls. The injuring ratings were based on the scale use in Test B. The results are shown in Table F.

Test D

Plastic tray liners with individual planting compartments were filled with planting medium and seeded with corn (*Zea mays*), soybean (*Glycine max.*), peanut (*A. hypogea*), tomato (*Lycopersium esenlentum*), gaint foxtail (*S. faberi*), guineagrass (*P. maximum*), Johnson grass (*S. halepense*), velvetleaf (*A. theophrasti*), morningglory, nightshade varieties—*Solanum nigrum, S. nigrum* subsp. nigrum. *S. ptycanthus* (green berries and black berries), *S. nigrum* subsp. schetesii and *S. nigrum* (atrazine tolerant).

The plantings were treated preemergence with Compound 6 formulated in a non-phytotoxic spray solution. Plants were visually rated at the enid of the test and compared with the appropriate controls. The injury ratings used in Test 8 were also employed in this test. The results are shown in Table G.

Test E

Rooted rough lemon cuttings were planted in 15-cm plastic pots. Another set of 11-cm plastic pots were filled with planting medium were seeded with balsam apple wine (*Momordica charantia*). sandbur (*C. echinatus*), pigweed (*Amaranthus viridus*) and guineagrass (*P. maximum*).

This citrus was sprayed to simulate the trunk-to-trunk herbicide application method used in citrus groves, the weeds were treated preemergence and the balsam apple wine treated both preemergence and postemergence. All pots were treated with Compound 6 formulated in a non-phytotoxic spray solvent. Plants were visually rated 21 and 65 DAT and compared with appropriate controls. The injury rating scale used in Test B was also used. The results are shown in Table H.

TABLE F

| Species | Compound 6 250 | 125 | 64 g/ha |
|---|---|---|---|
| | Preemergence | | |
| | 21 DAT | | |
| Peanut | 60 | 20 | 0 |
| Giant foxtail | 100 | 100 | 100 |
| Large crabgrass | 100 | 100 | 100 |
| Guineagrass | 100 | 100 | 100 |
| Johnson grass | 100 | 100 | 100 |
| Nightshade | 100 | 100 | 100 |
| Morningglory | 100 | 100 | 80 |
| Velvetleaf | 100 | 100 | 100 |
| | 40 DAT | | |
| Peanut | 40 | 20 | 0 |
| Giant foxtail | 100 | 100 | 100 |
| Large crabgrass | 100 | 100 | 100 |
| Guineagrass | 100 | 100 | 100 |
| Johnson grass | 100 | 100 | 90 |
| Nightshade | 100 | 100 | 100 |
| Morningglory | 100 | 100 | 80 |
| Velvetleaf | 100 | 100 | 100 |

TABLE G

| Species | Compound 6 64 | 32 | 16 | 8 | 4 g/ha |
|---|---|---|---|---|---|
| | Preemergence | | | | |
| Corn | 60 | 60 | 10 | 0 | 0 |
| Soybean | 70 | 40 | 0 | 0 | 0 |
| Peanut | 20 | 0 | 0 | 0 | 0 |
| Tomato | 100 | 100 | 100 | 100 | 90 |
| Giant foxtail | 100 | 100 | 100 | 90 | 40 |
| Guineagrass | 100 | 100 | 80 | 80 | 60 |
| Johnson rass | 100 | 90 | 30 | 20 | 20 |
| Velvetleaf | 100 | 100 | 100 | 100 | 100 |
| Morningglory | 50 | 30 | 20 | 0 | 0 |
| *Solanum nigrum* | 100 | 100 | 100 | 100 | 100 |
| *S. nigrum* | 100 | 100 | 100 | 100 | 100 |
| *S. nigrum* subsp. *nigrum* | 100 | 100 | 100 | 100 | 100 |
| *S. ptycanthus* (green berries) | 100 | 100 | 100 | 100 | 100 |
| *S. nigrum* subsp. *schetesii* | 100 | 100 | 100 | 100 | 100 |
| *S. ptycanthus* (black berries) | 100 | 100 | 100 | 100 | 100 |
| *S. nigrum* (atrazine tolerant) | 100 | 100 | 100 | 100 | 100 |

TABLE H

| | Compound 6 500 | 250 | 125 | 64 g a.i./ha |
|---|---|---|---|---|
| | 21 DAT | | | |
| Post directed | 0 | 0 | 0 | 0 |
| Citrus (rough lemon) | | | | |
| Preemergence | | | | |
| Balsam apple vine | 100 | 100 | 100 | 100 |
| Sandbur | 100 | 100 | 100 | 100 |
| Pigweed | 100 | 100 | 100 | 100 |
| Guineagrass | 100 | 100 | 100 | 100 |
| Postemergence | 100 | 100 | 100 | 100 |

TABLE H-continued

| | Compound 6 500 | 250 | 125 | 64 g a.i./ha |
|---|---|---|---|---|
| Balsam apple vine | | | | |
| | 65 DAT | | | |
| Post directed | 0 | 0 | 0 | 0 |
| Citrus (rough lemon) | | | | |
| Preemergence | | | | |
| Balsam apple vine | 100 | 100 | 100 | 100 |
| Sandbur | 100 | 100 | 100 | 100 |
| Pigweed | 100 | 100 | 100 | 100 |
| Guineagrass | 100 | 100 | 100 | 100 |
| Postemergence | 100 | 100 | 100 | 100 |
| Balsam apple vine | | | | |

What is claimed is:

1. A bicyclic imide of formula I

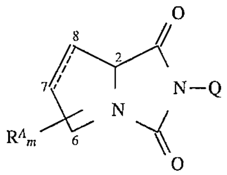

I wherein the bond linking C-7 and C-8 may be single or double;

m is 1–7;

$R^4$ can occupy one or more of the 2 or 6–8 positions and is independently selected from the group: hydroxy, halogen CN $OR^3$, $(C_1-C_4)$ alkyl, $S(O)_nR^3$, $COR^3$, and $C(O)SR^3$;

Q is

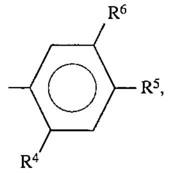

Q-1

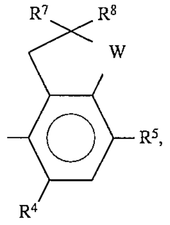

Q-2

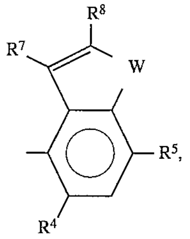

Q-3

-continued

Q-6

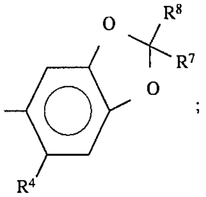

;

Q-7

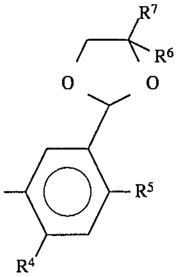

wherein $R^3$ is $(C_1–C_8)$alkyl, $(C_3–C_8)$cycloalkyl, $(C_3–C_8)$alkenyl, $(C_3–C_8)$alkynyl, $(C_1–C_8)$haloalkyl, $(C_2–C_8)$ alkoxyalkyl, $(C_2–C_4)$carboxy alkyl, $(C_3–C_8)$alkoxycarbonylalkyl, $(C_4–C_8)$alkenyloxyalkyl, $(C_4–C_8)$alkynyloxyalkyl, $(C_3–C_8)$haloalkoxyalkyl, $(C_3–C_8)$trialkylsilyl, $(C_3–C_8)$cyanoalkyl, $(C_3–C_8)$haloalkenyl, $(C_3–C_8)$haloalkynyl, $(C_2–C_8)$alkylcarbonyl, $(C_2–C_8)$alkoxycarbonyl, $(C_2–C_8)$haloalkoxycarbonyl, $P(O)(OR^{17})_2$, $CHR^{16}P(O)(OR^{17})_2$ or $CHR^{16}P(S)(OR^{17})_2$, phenyl or benzyl optionally substituted with halogen, $(C_1–C_3)$alkyl, $(C_1–C_3)$haloalkyl or $(C_1–C_4)$alkoxy;

$R^4$ is hydrogen or halogen;

$R^5$ is $(C_1–C_2)$alkyl, $(C_1–C_2)$haloalkyl, $OCH_3$, $SCH_3$, $OCHF_2$, halogen, CN or $NO_2$;

$R^6$ is hydrogen, $(C_1–C_8)$alkyl, $(C_1–C_8)$haloalkyl, halogen, $OR^{10}$, $S(O)_nR^{10}$, $COR^{10}$, $(O)SR^{10}$, $C(O)NR^{11}R^{12}$, CHO, $CH{=}CHCO_2R^{10}$, $CO_2N{=}CR^{13}R^{14}$, $NO_2$, CN, $NHSO_2R^{15}$ or $NHSO_2NHR^{15}$;

$R^7$ and $R^8$ are independently hydrogen, $(C_1–C_3)$alkyl, $(C_1–C_3)$haloalkyl or halogen; when Q is Q-2 or Q-6, $R^7$ and $R^8$ together with the carbon to which they are attached may be C=O;

$R^{10}$ is $(C_1–C_8)$alkyl, $(C_3–C_8)$ cycloalkyl, $(C_3–C_8)$alkenyl, $(C_3–C_8)$alkynyl, $(C_1–C_8)$haloalkyl, $(C_2–C_8)$alkoxyalkyl, $(C_2–C_6)$alkylthioalkyl, $(C_2–C_8)$alkylsulfinylalkyl, $(C_2–C_8)$alkylsulfonylalkyl, $(C_3–C_8)$alkoxyalkoxyalkyl, $(C_4–C_8)$cycloalkylalkyl, $(C_2–C_4)$carboxyalkyl, $(C_3–C_8)$alkoxycarbonylalkyl, $(C_6–C_8)$alkenyloxycarbonylalkyl, $(C_6–C_8)$alkynyloxycarbonylalkyl, $(C_6–C_8)$cycloalkoxyalkyl, $(C_4–C_8)$alkenyloxyalkyl, $(C_4–C_8)$alkynyloxyalkyl, $(C_3–C_8)$haloalkoxyalkyl, $(C_4–C_8)$haloalkenyloxyalkyl, $(C_4–C_8)$haloalkynyloxyalkyl, $(C_6–C_8)$cycloalkylthioalkyl, $(C_4–C_8)$alkenylthioalkyl, $(C_4–C_8)$alkynylthioalkyl, $(C_4–C_8)$trialkylsilylalkyl, $(C_3–C_8)$cyanoalkyl, $(C_3–C_8)$halocycloalkyl, $(C_3–C_8)$haloalkenyl, $(C_5–C_8)$alkoxyalkenyl, $(C_5–C_8)$haloalkoxyalkenyl, $(C_5–C_8)$alkylthioalkenyl, $(C_3–C_8)$haloalkynyl, $(C_5–C_8)$alkoxyalkynyl, $(C_5–C_8)$haloalkoxyalkynyl, $(C_5–C_8)$alkylthioalkynyl, $(C_2–C_8)$alkylcarbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1–C_4)$alkyl substituted with phenoxy or benzyloxy optionally substituted with halogen, $(C_1–C_3)$alkyl or $(C_1–C_3)$haloalky; benzyl optionally substituted with halogen, $(C_1–C_3)$alkyl or $(C_1–C_3)$haloalkyl; or phenyl optionally substituted with halogen, $(C_1–C_3)$alkyl, $(C_1–C_3)$haloalkyl or $(C_1–C_4)$alkoxy;

$R^{11}$ and $R^{13}$ are independently hydrogen or $(C_1–C_4)$alkyl;

$R^{12}$ and $R^{14}$ are independently $(C_1–C_4)$alkyl, or phenyl optionally substituted with halogen, $(C_1–C_3)$alkyl, $(C_1–C_3)$haloalkyl or $(C_1–C_4)$alkoxy;

$R^{11}$ and $R^{12}$ may be taken together as $—(CH_2)_5—$, or $—(CH_2)_4—$, in which optionally one or more H-atoms may be replaced by $(C_1–C_3)$alkyl, phenyl or benzyl;

$R^{13}$ and $R^{14}$ may be taken together with the carbon to which they are attached to form $(C_3–C_l)$cycloalkyl;

$R^{15}$ is $(C_1–C_4)$alkyl or $(C_1–C_4)$haloalkyl;

$R^{16}$ is hydrogen or $(C_1–C_3)$alkyl;

$R^{17}$ is $(C_1–C_6)$alkyl, $(C_3–C_6)$alkenyl Or $(C_3–C_6)$alkynyl;

W is 0 or S;

n is 0, 1 or 2;

provided that when Q is not fused to a ring bridging the 5'- and 6'-position and C-7 and C-8 are linked by a single bond, then at least one $R^A$ is other than hydroxy, halogen, $(C_1–C_4)$alkyl, $(C_1–C_4)$ alkoxy.

2. A bicyclic imide selected from the group consisting of 4-[4'-chloro-2'-fluoro-5'-(prop-2-ynyloxy)phenyl]-3,5-dioxo-7-fluoro-1,4-diazobicyclo-[3.3.0]octane, 4-[4'-chloro-2'-fluoro-5'-(1-methyl-prop-2-ynyloxy)phenyl]-3,5-dioxo-7-fluoro-1,4-diazabicyclo[3.3.0]octane, 4-[4'-chloro-2'-fluoro-5'-(2-propynyloxy)phenyl]-3,5-dioxo-7-chloro-1,4-diazabicyclo[3.3.0]octane, 4-[4'-chloro-2'-fluoro-5'-(1-methylethoxy)phenyl]-3,5-dioxo-7,7-difluoro-1,4-diazabicyclo[3.3.0]octane and any stereoisomer thereof.

3. A bicyclic imide according to claim 1 or 2, characterized in that at least one $R^A$ is in the 7-position.

4. A bicyclic imide according to claim 3, characterized in that at least one $R^A$ in the 7-position is fluoro, chloro or bromo.

5. A bicyclic imide according to any one of claims 1 to 4, characterized in that it has 2R-configuration.

6. A composition for controlling weeds comprising an effective amount of a compound of claim 1 or 2 and at least one carrier therefor.

7. A method for controlling weeds comprising applying to the locus to be protected an effective amount of a compound of claim 1 or 2.

8. A method for controlling weeds in plantation crops comprising applying to the locus to be protected an effective amount of a compound of formula Ia:

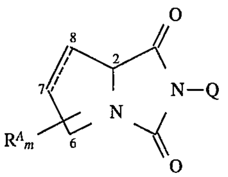

Ia wherein the bond linking C-7 and C-8 may be single or double;

m is 1–7;

$R^A$ can occupy one or more of the 2 or 6–8 positions and is independently selected from the group: hydroxy, halogen, CN, $OR^3$, $(C_1–C_4)$alkyl, $S(O)_nR^3$, $COR^3$, and $C(O)SR^3$;

Q is

Q-1

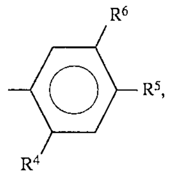

Q-2

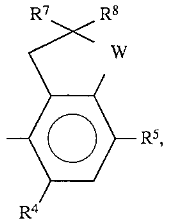

Q-3

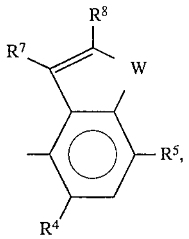

Q-6

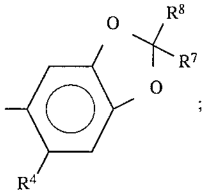

;

Q-7

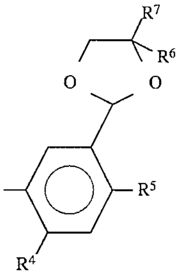

wherein $R^3$ is $(C_1-C_8)$alkyl, $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_4)$carboxy alkyl, $(C_3-C_8)$alkoxycarbonylalkyl, $(C_4-C_8)$alkenyloxyalkyl, $(C_4-C_8)$alkynyloxyalkyl, $(C_3-C_8)$haloalkoxyalkyl, $(C_3-C_8)$trialkylsilyl, $(C_3-C_8)$cyanoalkyl, $(C_3-C_8)$haloalkenyl, $(C_3-C_8)$haloalkynyl, $(C_2-C_8)$alkylcarbonyl, $(C_2-C_8)$alkoxycarbonyl, $(C_2-C_8)$haloalkoxycarbonyl, P(O))$(OR^{17})_2$, $CHR^{16}P(O)(OR^{17})_2$ or $CHR^{16}P(S)(OR^{17})_2$, phenyl or benzyl optionally substituted with halogen, $(C_1-C_3)$alkyl, $(C_1-C_3)$haloalkyl or $(C_1-C_4)$alkoxy;

$R^4$ is hydrogen or halogen;

$R^5$ is $(C_1-C_2)$alkyl, $(C_1-C_2)$haloalkyl, $OCH_3$, $SCH_3$, $OCHF_2$, halogen, CN or $NO_2$;

$R^6$ i s hydrogen, $(C_1-C_8)$alkyl, $(C_1-C_8)$haloalkyl, halogen, $OR^{10}$, $S(O)_nR^{10}$, $COR^{10}$, $C(O)SR^{10}$, $C(O)NR^{11}R^{12}$, CHO $CH{=}CHCO_2R^{10}$, $CO_2N{=}CR^{13}R^{14}$, $NO_2$, CN, $NHSO_2R^{15}$ or $NHSO_2NHR^{15}$;

$R^7$ and $R^8$ are independently hydrogen, $(C_1-C_3)$alkyl, $(C_1-C_3)$haloalkyl or halogen; when Q is Q-2 or Q-6, $R^7$ and $R^8$ together with the carbon to which they are attached may be C═O;

$R^{10}$ is $(C_1-C_8)$alkyl $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_6)$alkylthioalkyl, $(C_2-C_8)$alkylsulfinylalkyl, $(C_2-C_8)$alkylsulfonylalkyl, $(C_3-C_8)$alkoxyalkoxyalkyl, $(C_4-C_8)$cycloalkylalkyl, $(C_2-C_4)$carboxyalkyl, $(C_3-C_8)$alkoxycarbonylalkyl, $(C_6-C_8)$alkenyloxycarbonylalkyl, $(C_6-C_8)$alkynyloxycarbonylalkyl, $(C_6-C_8)$cycloalkoxyalkyl, $(C_4-C_8)$alkenyloxyalkyl, $(C_4-C_8)$alkynyloxyalkyl, $(C_3-C_8)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_3-C_8)$cyanoalkyl, $(C_3-C_8)$halocycloalkyl, $(C_3-C_8)$haloalkenyl, $(C_5-C_8)$alkoxyalkenyl, $(C_5-C_8)$haloalkoxyalkenyl, $(C_5-C_8)$alkylthioalkenyl, $(C_3-C_8)$haloalkynyl, $(C_5-C_8)$alkoxyalkynyl, ]$(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}$ $P(O)(OR^{17})_2$, $P(O)(OR^{17})_2$, $CHR^{16}P(S)(O)R^{17})_2$, $CHR^{16}C(O)NR^{11}R12$, $CHR^{16}C(O)NH_2$, $(C_1-C_4)$alkyl substituted with phenoxy or benzyloxy optionally substituted with halogen, $(C_1-C_3)$alkyl or $(C_1-C_3)$haloalkyl; benzyl optionally substituted with halogen, $(C_1-C_3)$alkyl or $(C_1-C_3)$haloalkyl; or phenyl optionally substituted with halogen, $(C_1-C_3)$alkyl, $(C_1-C_3)$haloalkyl Or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, or phenyl optionally substituted with halogen, $(C_1-C_3)$alkyl, $(C_1-C_3)$haloalkyl or $(C_1-C_4)$alkoxy;

$R^{11}$ and $R^{12}$ may be taken together as $—(CH_2)_5—$, or $—(CH_2)_4—$ in which optionally one or more H-atoms may be replaced by $(C_1-C_3)$alkyl, phenyl or benzyl;

$R^{13}$ and $R^{14}$ may be taken together with the carbon to which they are attached to form $(C_3-C_8)$cycloalkyl;

$R^{15}$ is $(C_1-C_4)$alkyl or $(C_1-C_4)$haloalkyl;

$R^{16}$ is hydrogen or $(C_1-C_3)$alkyl;

$R^{17}$ is $(C_1-C_6)$alkyl, $(C_3-C_6)$alkenyl or $(C_3-C_6)$alkynyl;

W is 0 or S;

n is 0, 1 or 2.

9. A method of claim 8 wherein the plantation crop is selected from the group consisting of citrus, sugarcane, coffee, banana, oil palm, grapes and rubber.

10. A method of claim 8 or 9 employing at least one of the compounds of the group consisting of 4-[4'-chloro-2'-fluoro-5'-(1-methylethoxy)phenyl]-3,5-dioxo-7-fluoro-1,4-diazabicyclo[3.3.0]octane, 4-[4'-chloro-2'-fluoro-5'-(1-methylprop-2-ynyloxy)phenyl]-3,5-dioxo-7-fluoro-1,4-diazabicyclo[3.3.0]octane, 4-[4'-chloro-2'-fluoro-5'-(prop-2-ynyloxy)phenyl]-3,5-dioxo-7-fluoro-1,4-diazabicyclo[3.3.0]octane, 4-[4'-chloro-2'-fluoro-5'-(1-methylethoxy)phenyl]-3,5-dioxo-7,7-difluoro-1,4-diazabicyclo[3.3.0]octane, 6-fluoro-2-(7-fluoro-3-oxo-4-prop-2-ynyl-3,4-dihydro-2H-benzo[1,4]oxazin-6-yl)-tetrahydropyrrolo[1,2-c]imidazole-1,3-dione, 6,6-difluoro-2-(7-fluoro-3-oxo-4-prop-2-ynyl-3,4-dihydro-2H-benzo[1,4]oxazin-6-yl)-tetrahydropyrrolo[1,2-c]imidazole-1,3-dione (JUPAC), 4-[2-chloro-4-fluoro-5-(6-fluoro-1,3-dioxotetrahydropyrrolo[1,2-c]imidazol-2-yl)phenoxy]but- 2-enoic acid methyl ester (JUPAC) and any stereoisomer thereof.

11. A method of claim 8 wherein the crop is peanut and the compound is applied preemergence.

* * * * *

UNITED STATES PATENT AND TRADEMARK OFFICE
CERTIFICATE OF CORRECTION

PATENT NO. : 5,605,877
DATED : February 25, 1997
INVENTOR(S) : Kofi Sam Amuti et al.

It is certified that error appears in the above-identified patent and that said Letters Patent is hereby corrected as shown below:

Column 56, line 36, change "halogen $CNOR^3$" to --halogen, CN, $OR^3$--.

Column 58, line 16, change "($C_3$-$C_1$) cycloalkyl" to --($C_3$-$C_8$) cycloalkyl--.

Signed and Sealed this

Eighth Day of June, 1999

Attest:

Q. TODD DICKINSON

*Attesting Officer*

*Acting Commissioner of Patents and Trademarks*